United States Patent [19]
Schenck

[11] 4,317,041
[45] Feb. 23, 1982

[54] MULTICHAMBER PHOTOREACTOR

[76] Inventor: Günther O. Schenck, Bismarckstrasse 31, 433 Mülheim, Fed. Rep. of Germany

[21] Appl. No.: 155,580

[22] Filed: Jun. 2, 1980

Related U.S. Application Data

[62] Division of Ser. No. 923,710, Jul. 11, 1978, Pat. No. 4,255,283.

[30] Foreign Application Priority Data

Aug. 6, 1977 [DE] Fed. Rep. of Germany ....... 2735550

[51] Int. Cl.³ .......................................... G01M 21/01
[52] U.S. Cl. ................. 250/435; 250/432 R; 250/436
[58] Field of Search ............... 250/432, 435, 436, 437

[56] References Cited

U.S. PATENT DOCUMENTS

| | | | |
|---|---|---|---|
| 1,193,143 | 8/1916 | Hellbronner et al. | 250/437 |
| 1,896,375 | 2/1933 | Ross | 250/432 |
| 1,969,655 | 8/1934 | Mailey | 250/435 |
| 2,669,661 | 2/1954 | Riddiford et al. | 250/436 |
| 3,079,498 | 2/1963 | Ruffin | 250/437 |
| 3,433,946 | 3/1969 | Harwick | 250/438 |
| 3,471,693 | 10/1969 | Veloz | 250/432 |
| 3,562,520 | 2/1971 | Hippen | 250/432 |
| 3,767,918 | 10/1973 | Graybeal | 250/436 |
| 3,854,875 | 12/1974 | Bosshardt | 250/432 |

Primary Examiner—Harold A. Dixon
Attorney, Agent, or Firm—Darbo & Vandenburgh

[57] ABSTRACT

Various embodiments of photoreactors are disclosed which have at least two irradiation chambers with a window therebetween. Ultraviolet radiation is introduced into one of the chambers at a side opposite the window so that it passes through that chamber, through the window and into the other chamber. The fluid medium to be purified is passed through the chambers and subjected to the radiation while in the chambers. The flow of the medium is through the chambers in series in some embodiments and in parallel in others. An embodiment is disclosed wherein a recirculation line is established around the reactor with the recirculation being continuous or intermittent. When intermittent the purified fluid medium also is drawn off intermittently, between the periods of recirculation. In some embodiments the amount of radiation traversing all the chambers is monitored. If the monitored amount drops below a given amount, the apparatus is shut down. Alternatively, the rate of flow of the medium is adjusted, based on that monitored amount, with the rate of flow increasing or decreasing, respectively, in response to increases or decreases in that amount.

32 Claims, 20 Drawing Figures

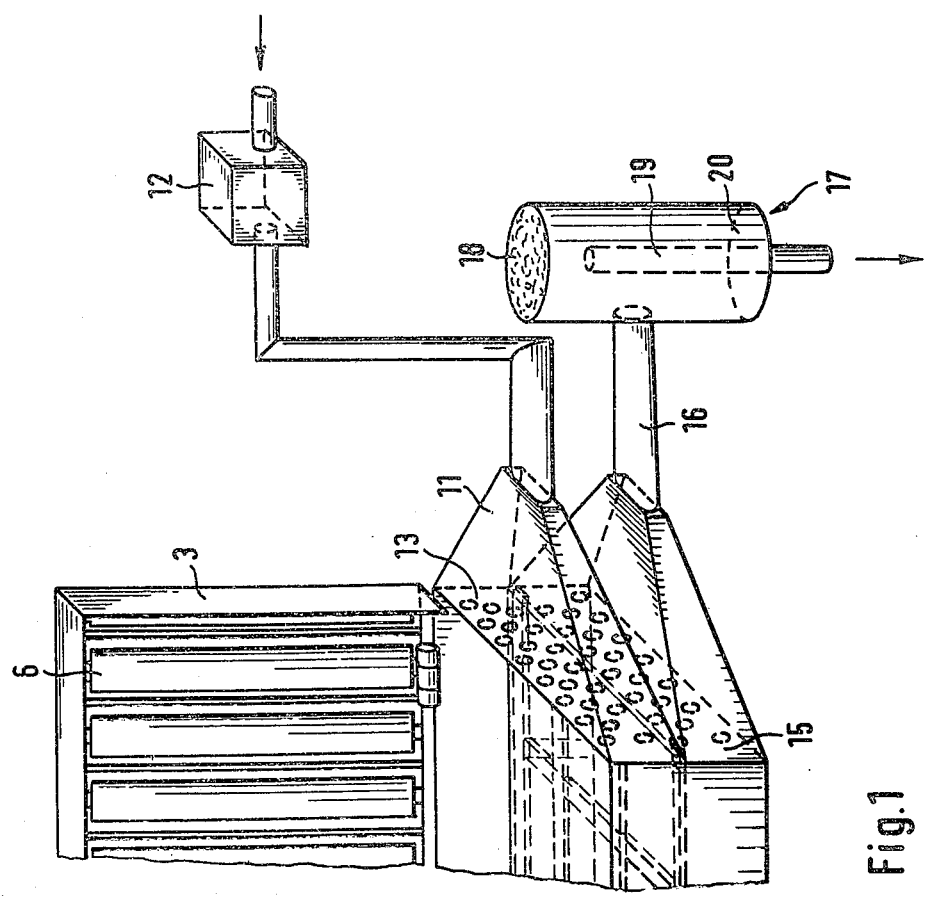
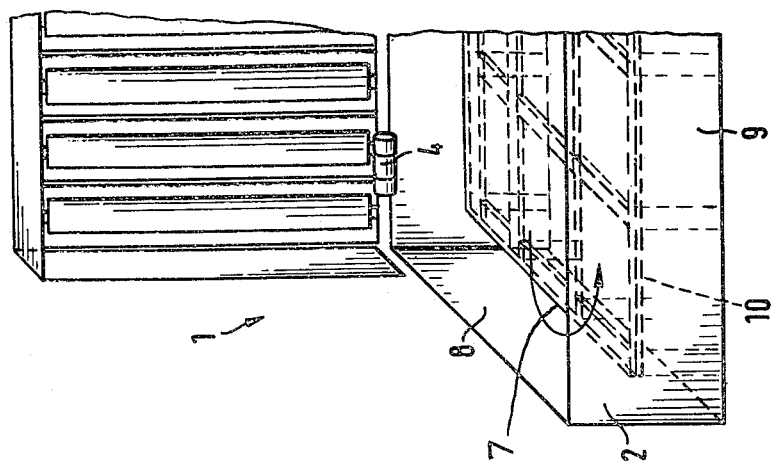
Fig.1

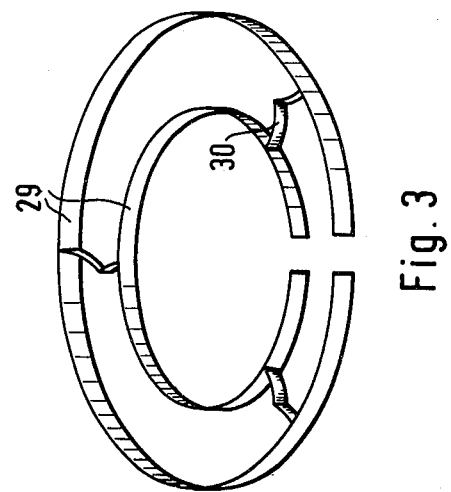
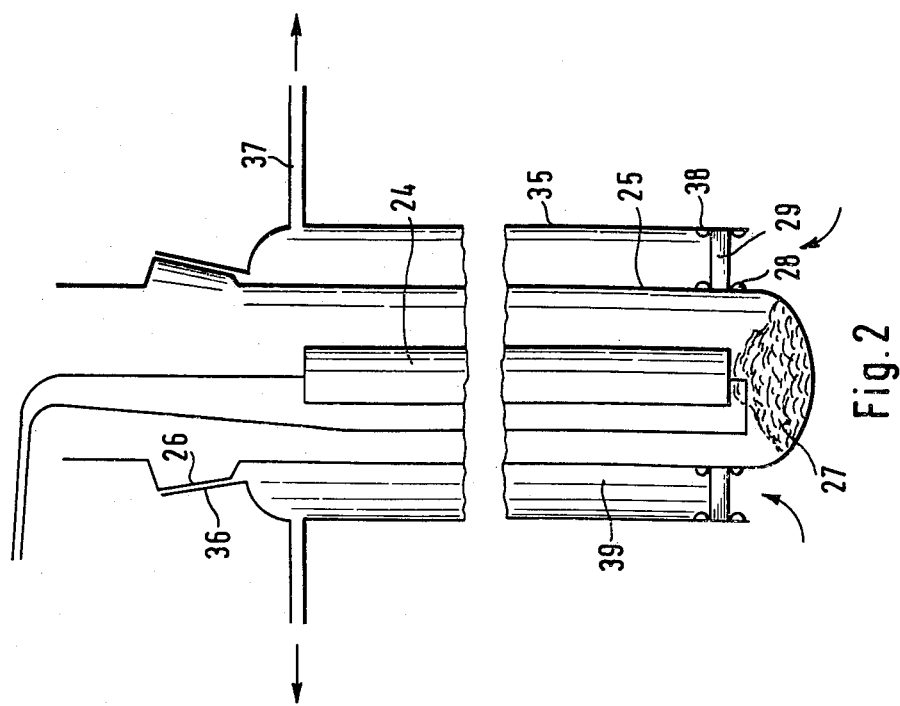

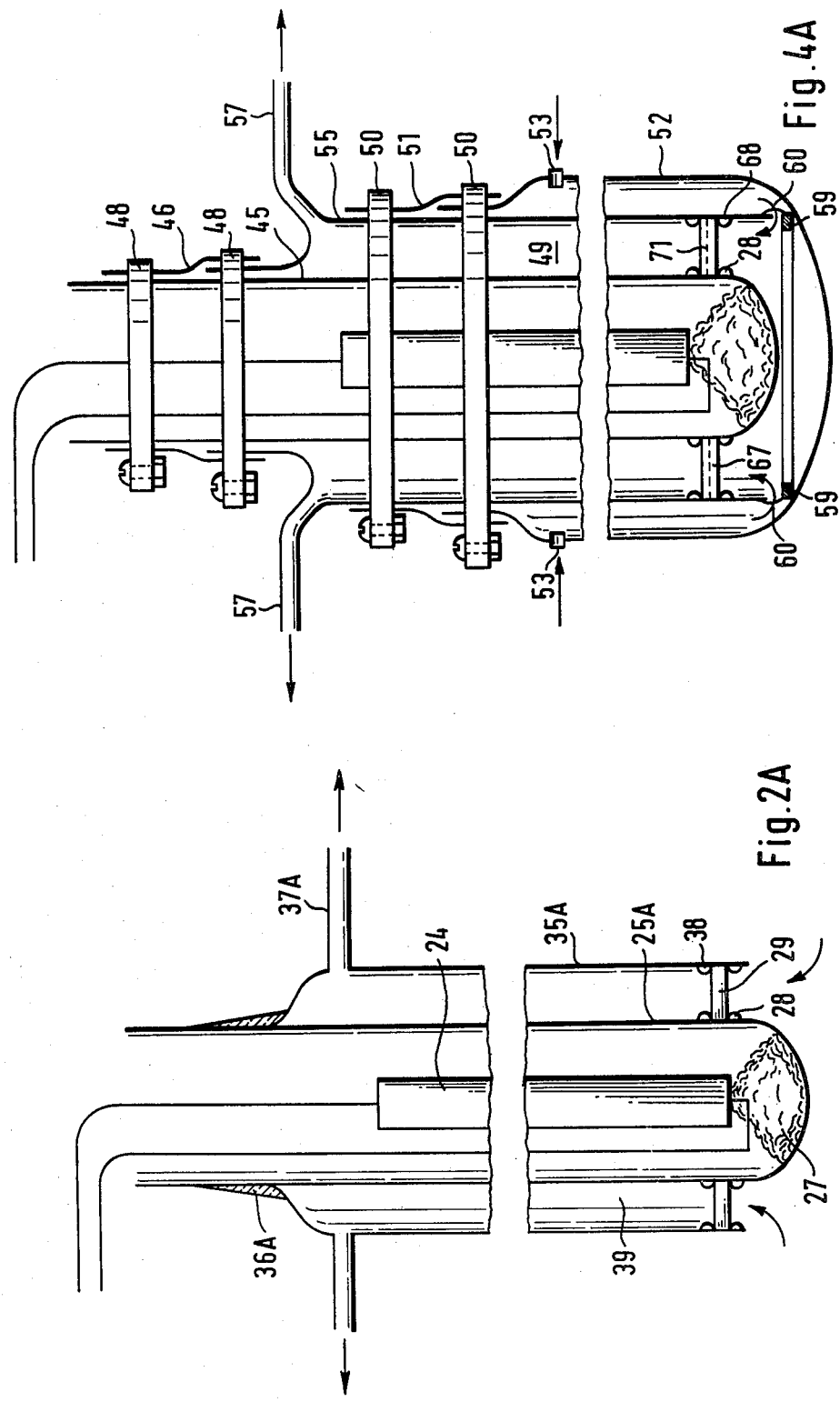

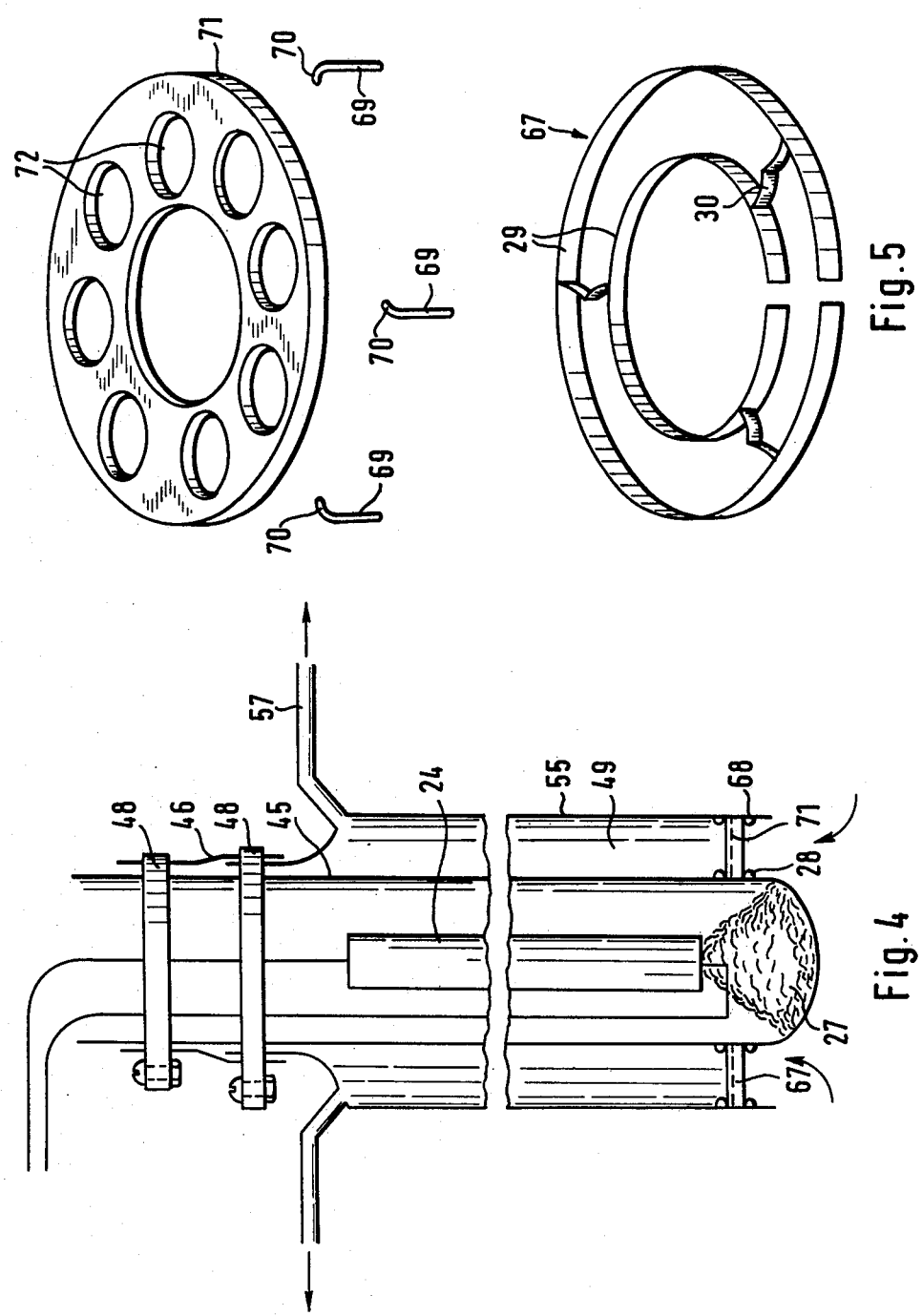

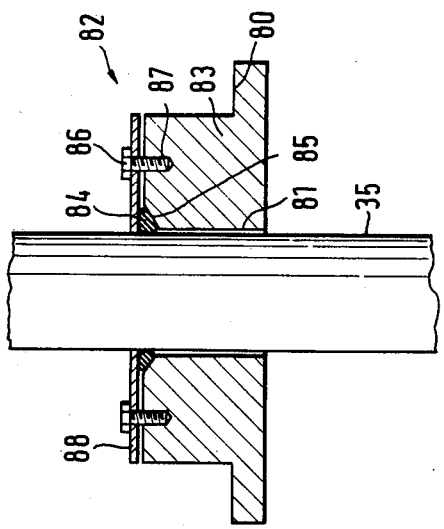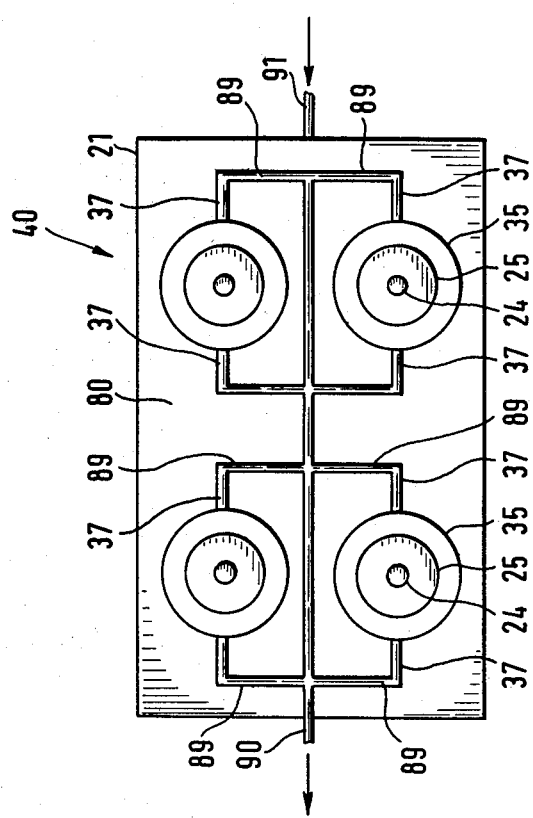

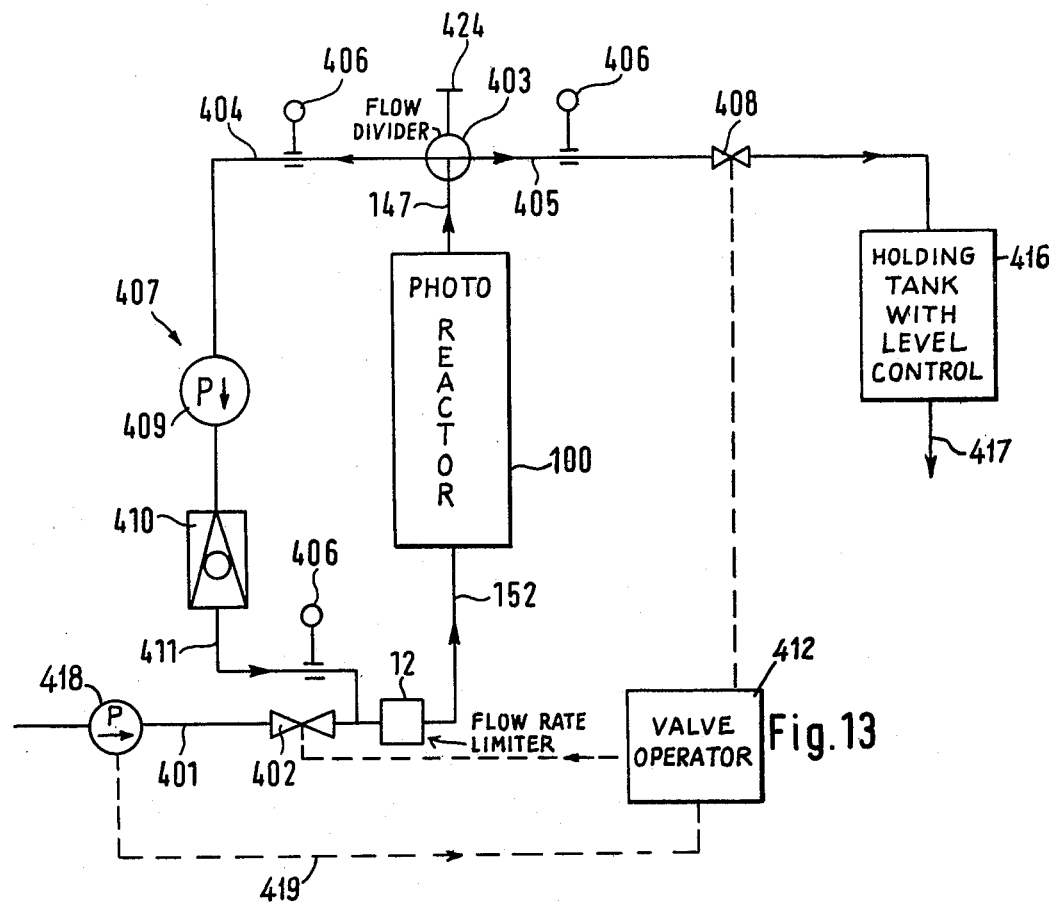
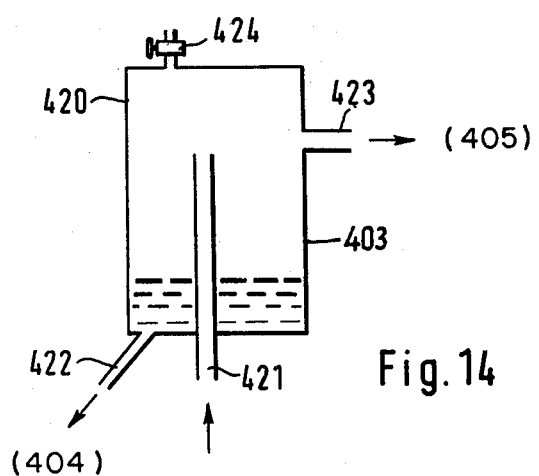
Fig.13
Fig.14

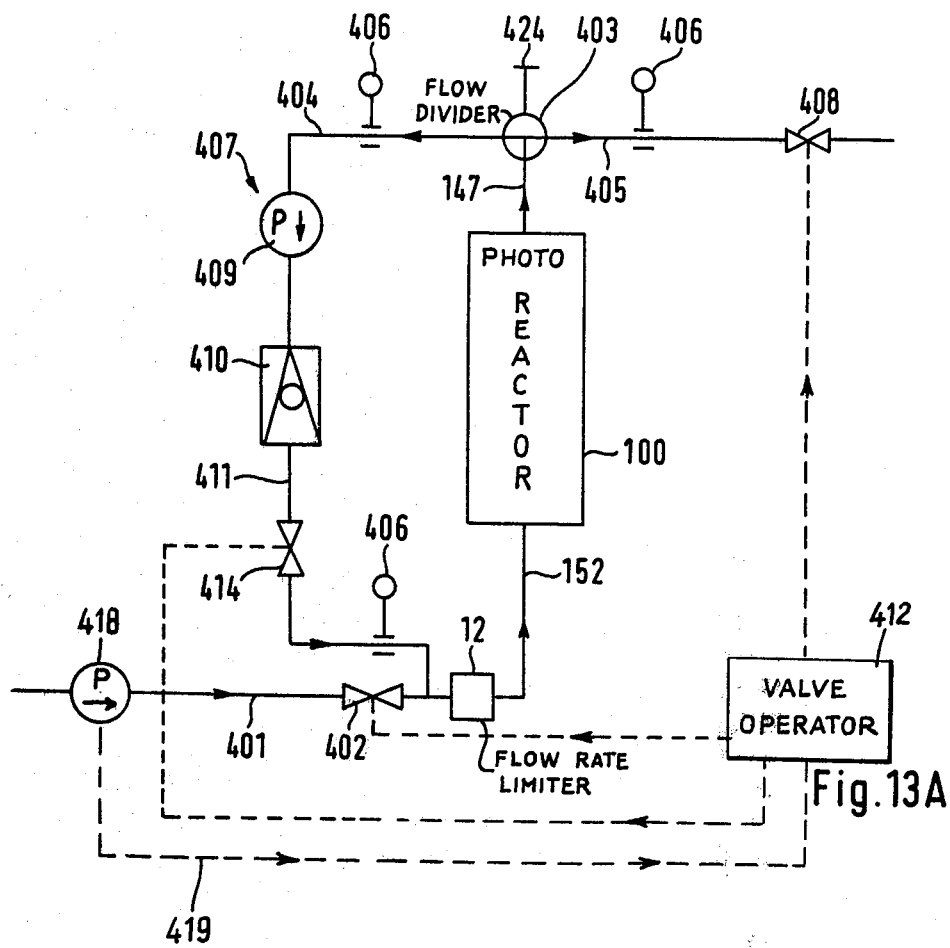

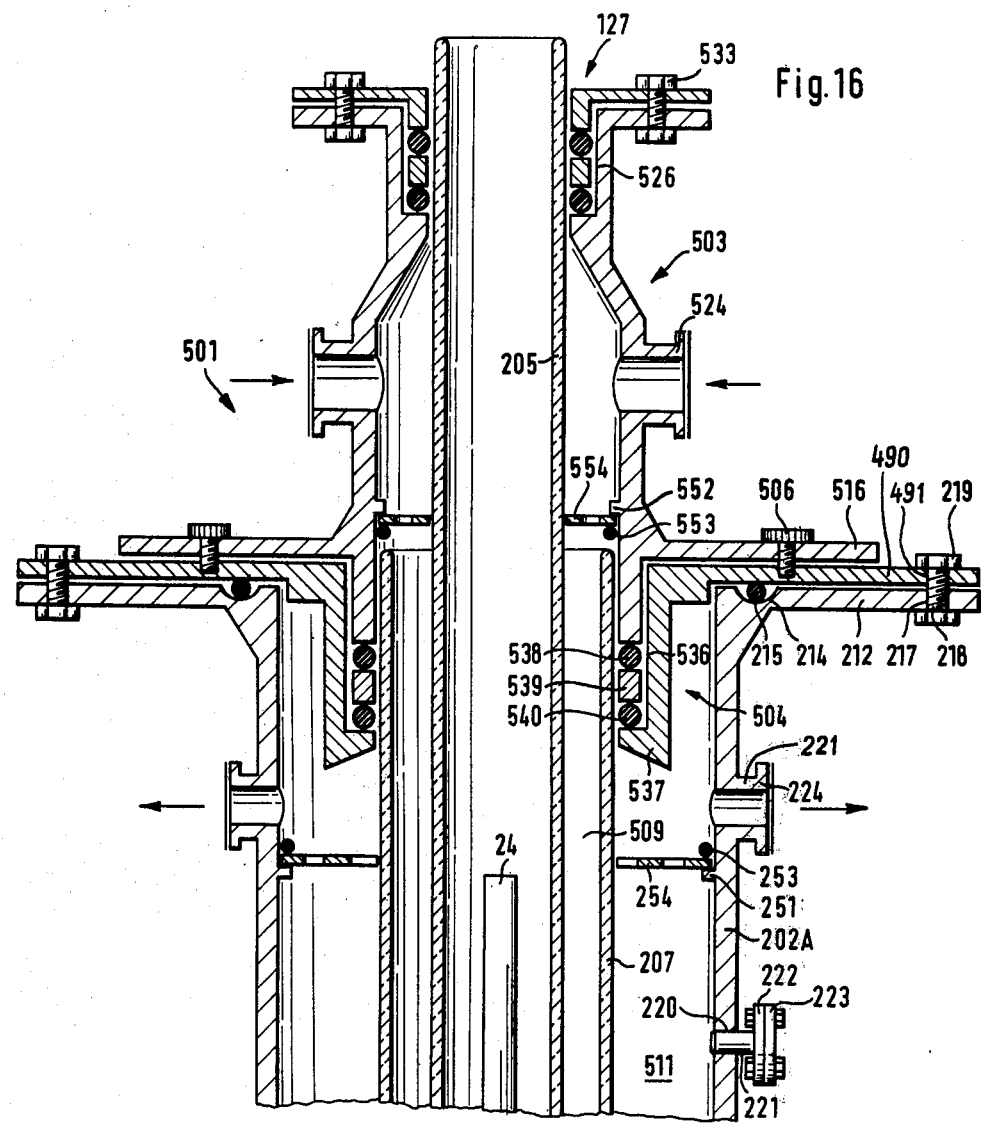

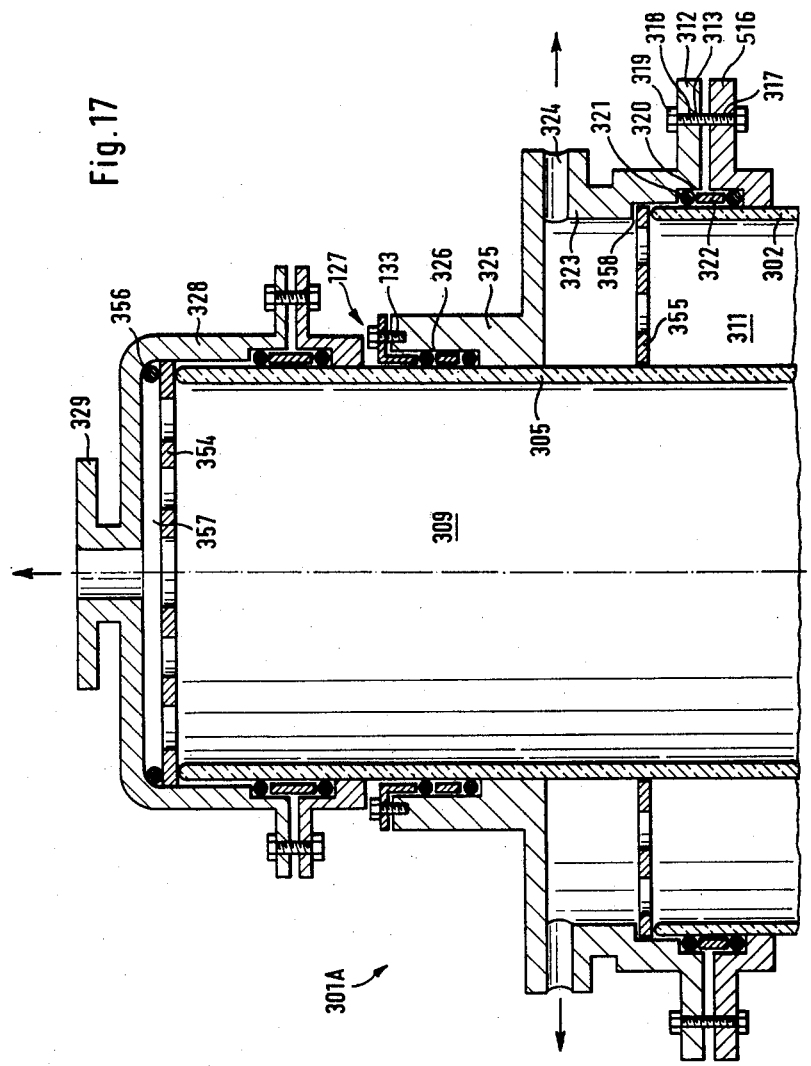

MULTICHAMBER PHOTOREACTOR

RELATED APPLICATION

This is a division of application Ser. No. 923,710, filed July 11, 1978, now U.S. Pat. No. 4,255,283.

BACKGROUND AND SUMMARY OF THE INVENTION

The invention relates to a process for purifying, particularly for sterilizing or disinfecting fluid media in flow reactors by irradiating with a predetermined minimum irradiation dose of ultraviolet radiation predominantly in the wavelength range between 240 and 320 nm. The invention also relates to apparatus for carrying out such a process including a source of radiation comprising at least one lamp emitting ultraviolet radiation in the wavelength range between 240 and 320 nm, comprising further a flow reactor associated therewith and equipped with means to conduct the medium to be irradiated to and from said reactor and finally comprising monitoring equipment to monitor the ultraviolet radiation passing through said flow reactor.

Processes and apparatus for pufifying, particularly for sterilizing or disinfecting, by the use of ultraviolet rays are employed with advantage over chemical agents for removing from water pathogenic, toxical or otherwisely undesirable bodies sensitive towards ultraviolet radiation. Such undesirable bodies may constitute microorganisms like bacteria, spores, yeasts, or fungi, algae, etc., including viruses or bacteriophages. They also may constitute cancerogenic aromatic compounds, numerous halogen compounds, and most of all chlorine compounds, for instance chlorinated phenols, etc., which will represent impurities burdening the environment. Irradiation of this kind may be employed in connection with the preparation of potable water and it is particularly useful in combination with ion exchange and inverse osmosis plants. Also swimming pool water can be disinfected to the hygienic degree of potable water. Ultraviolet irradiation processes also may be used to treat water circulating for instance in air conditioning units (of the direct air-water contact type) of hospitals. Thus substantially higher degrees of disinfection as required for potable water may be obtained which is a prerequisite of use for instance in connection with opthalmologic preparations or for washing purposes in hospital operating rooms. Further applications will be found for example in breweries and in beverage production, in the food, pharmaceutical and cosmetics industries, photo and electronics industries, in sewage purification, and in the preparation of very high purity seawater for biotechnical purposes.

Photochemical sterilization, disinfection, and detoxication, respectively, follows the known basic principles of photochemical reactions, the validity of which will have to be observed in conducting such reactions in practice. Generally, concentrations of pathogenic and other impurities to be removed by ultraviolet irradiation are relatively low. In practice, the absorption in the medium to be irradiated is therefore determined by other ingredients, the absorption by which competes with that by the microorganisms, etc. In use, it is desirable that the available photon flux should be utilized to the greatest possible extent. Generally chamber depths at which 90% of the incident photons are absorbed will suffice therefor, since doubling of the depth only will result in the further absorption of an additional 9% of the incoming photons. In ultraviolet sterilization techniques depths characterized by 90% absorption are denoted as the "effective depth of penetration". At the wavelength of 254 nm said depth may amount to a multiple of 10 cm (about 4 in.) in particulary pure water, but only to fractions of a millimeter (about 0.04 in.) in milk.

In ultraviolet irradiations in which an extent of 90 to 99% conversion (inactivation) of the microorganisms or, respectively, of the initial impurity present, is achieved there will exist approximately an exponential time dependence as in kinetically analogous photochemical reactions. The aforementioned extent of 90 to 99% conversion will occur within a fraction of the time of that usually required for sterilization or, respectively, detoxication reactions. In such instances the absolute extent of the conversion achieved which will asymptotically approach the initial germ number (numbers of germs per unit volume) may not be of interest. Of much greater interest will be the amount of purified medium of the required degree of purification (as, for instance, $10^{-6}$) obtainable. It will thus be seen that operating at a chamber depth corresponding to 90% absorption, i.e., at the so-called effective depth of penetration, as suggested by photochemical considerations will not produce optimum results. Because of the exponential Lambert law of absorption there will occur an inhomogeneous distribution of purification rates through the depth of irradiation. Since with the presently employed low powered radiation sources the irradiated medium will have a predominantly laminar flow characteristic in passing through the flow reactor, a logarithmic distribution of purification rates will develop within said flow reactor with predominance of the substantially lower purifications at greater distances from the radiation source.

For killing (inactivation) of microorganisms as an example of a purification in the dosage range as required in water disinfection, the simple dose-effect principle will hold approximately. Accordingly, the input concentration of microorganisms (initial number per milliliter) $N_0$ will become reduced by a dose $E \cdot t$ ($E=$ irradiation intensity; $t=$ period of irradiation) to the concentration of microorganisms $N_t$ at time t in accordance with a sensitivity constant k characteristic for the respective species, to wit:

$$N_t = N_0 \cdot 10^{-E \cdot t \cdot k}$$

With the incoming radiation directed in parallel, the irradiation intensity E itself will become exponentially reduced with increasing depth of the irradiated medium in accordance with the Lambert Beer law of absorption. Altogether, therefore, the following relation will result for the reduction of germ number $N_t$ after irradiation time t:

$$N_t = N_0 \cdot 10^{-k \cdot t \cdot G \cdot E \cdot 10^{-\alpha d}}$$

wherein $\alpha$ represents the logarithmic absorption factor of the medium irradiated and d the depth thereof as measured parallel to the path of radiation. With nonparallel incident radiation an additional alteration of radiation intensity will occur in accordance with the geometry of the flow reactor which alteration is accounted for in the aforementioned equation by the corresponding geometry factor G.

In a known photoreactor with approximately parallel incidence of radiation the radiation source is positioned, in a reflector, above the surface of the medium to be irradiated (M. Luckiesh, Applications of Germicidal, Erythemal, and Infrared Energy, Van Nostrand, New York, 1946, pages 257-265; Company brochure LS-179, General Electric Company, "Germicidal Lamps and Applications"). Photoreactors of such a kind may only be used in connection with freely flowing media, however, and not in pressurized systems in which the medium to be irradiated is passed through the photoreactor under pressure. An annular design has been suggested for photoreactors of the latter kind with the radiation source being disposed within the interior annulus space; the radiation source may then be a high pressure mercury lamp (W. Busch, Water Sterilizer "Uster", AEG-Mitteilungen 1936, No. 5, pages 178-181). But also low pressure mercury lamps (K. Wuhrmann, "Disinfection of Water by Means of UV Irradiation", Gas/Wasser/-Wärme 1960, Vol. 14, pages 100-102) and bundles thereof (P. Ueberall, "Chemicalfree Disinfection of Potable and Service Water by Ultraviolet Rays"; Die Stärke 1969, Vol. 21, pages 321-327) have been employed. To compensate for the strong decrease in irradiation intensity because of the Lambert law of absorption and of the photoreactor geometry in annular photoreactors it has been proposed to utilize a number of lamps for the radiation source, each lamp being disposed in a respective reflector, and with the reflectors concentrically surrounding the exterior of the annular flow reactor (German Offenlegungsschrift No. 2119961). Also additional lamps may be used in the interior space (German Offenlegungsschrift 2205598). In the group of photoreactors having radiation sources with radially directed emission there are also included photoreactors having single or multiple radiation sources in an immersion type arrangement in a suitable tank through which the medium to be irradiated flows (L. Grün, M. Pitz; "UV Rays in Jet Chambers and Air Passages of Air Conditioning Equipment in Hospitals", Zbl. für Hygiene, I. Abteilung Orig. 1974, Vol. B159, pages 50-60).

Although effective depths of penetration with 90% absorption are known for many media, known photoreactors generally provide for depths of just a fraction thereof. For disinfecting potable water on sea-going vessels there even exists a regulation according to which the depth of the medium to be irradiated is not permitted to exceed 7.62 cm (3 in.; Department of Health, Education and Welfare, Public Health Service; Division of Environmental Engineering and Food Protection; "Policy Statement on Use of the UV Process for Disinfection of Water"; Apr. 1, 1966). While such a requirement may be significant for safety reasons, it results in loss of the opportunity for economic disinfection in many cases of media having high transmission factors since a substantial portion of the photon energy entering the medium is not actually utilized and is lost in the photoreactor walls. Attempts to salvage the unused portion by providing reflective walls have not proven particularly effective.

On irradiating (parallel incidence) at a depth of 90% absorption at such a high dosage that disinfection within the first layer encompassing 10% absorption reaches values of at least $10^{-10}$ an inhomogeneity of disinfection degrees in accordance with the foregoing equation will result covering the range of $10^{-9}$ in the closest layer to $10^{-1}$ in the most remote layer. An average value of the order of $10^{-2}$ will then be obtained for the degree of disinfection which is of little satisfaction considering that the theoretically obtainable degree of disinfection will be in the order of $10^{-4}$ as calculated with the assumption of a non-logarithmically decreasing mean radiation intensity.

The object to be achieved by the present invention accordingly is to provide a process and apparatus which will permit optimum utilization of the ultraviolet radiation as emitted from the radiation source at as high a throughput of the fluid medium as possible.

This object is achieved by the present invention in passing the medium through separate irradiation chambers of a flow reactor subdivided at right angles with respect to the general flow direction (path) of the radiation and by having portions of the radiation incident in the first irradiation chamber, i.e., the chamber closest to the radiation source, pass into at least the directly adjoining irradiation chamber.

The invention starts from recognizing that by subdividing the photoreactor the depth of each irradiation chamber may be selected in such a way that the variation in radiation intensity through the depth of the respective chamber does not too unfavorably affect the economy of the irradiation process. Thereby the distribution of the degree of disinfection through each respective irradiation chamber will become less inhomogeneous. Quadruple or quintuple subdivision of a depth providing 90% overall absorption may result in differences between the degree of disinfection within each irradiation chamber of less than 3 orders of magnitude, while such differences may encompass more than 8 orders of magnitude in a nondivided photoreactor. The principle of the invention is thus seen to be based on adjusting the efficiency of the photoreactor, which passes through an optimum with increasing depth and then strongly decreases, in such a way as to operate at a depth of only fractional absorption, utilizing the photons issuing therefrom in adjoining chambers of similar or the same depth also providing for only fractional absorption. The favorable effect as obtained by the subdivision is widely independent of the irradiation geometry of the respective photoreactor. Such effect will be achieved as well in photoreactors with a radiation source of the immersion type arrangement as in annular photoreactors with the radiation source disposed in the interior space and/or externally thereof. The effect will also be realized in photoreactors of the type in which the radiation source is positioned above the surface of the medium.

It has been found on closer analysis that the economy of the irradiation process is particularly strongly affected in the negative by the inhomogeneity of the disinfection degree in those layers of the irradiated medium which are exposed to the highest irradiation intensity. For utilizing, on the one hand, as much as possible of the high radiation intensity prevailing immediately adjacently to the radiation source which is specifically efficient in the disinfection and, on the other hand, for suffering as little loss as possible on this favorable effect by the inhomogeneity in the distribution of degrees of disinfection, absorption in the irradiation chamber immediately adjacent to the radiation source should not exceed 60% of the incoming radiation.

Advantageously at least 50% of the radiation entering into the medium present in the irradiation chamber immediately adjacent to the radiation source will enter into the directly adjoining irradiation chamber (that is, not more than 50% of the incident radiation being absorbed in said medium present in said irradiation chamber immediately adjacent to said radiation source); in a flow reactor having up to 5 irradiation chambers not more than $(1-0.5^n) \cdot 100$ percent of the totally incident radiation should become absorbed, wherein n represents the number of irradiation chambers. It is not necessary, however, that the incident radiation become attenuated by the same fraction in each respective irradiation chamber. In keeping with the foregoing discussion the efficiency of the purification or disinfection, respectively, is determined by the radiation intensity gradient existing between incident and emergent radiation in each respective irradiation chamber. This will hold for each single irradiation chamber in a multichamber photoreactor so that in the case of, for instance, two irradiation chambers the total absorption of the incident radiation should not exceed 75% to keep said gradient sufficiently small with respect to each single irradiation chamber and to maintain as high an overall efficiency as possible.

An effort has already been made, in connection with a single chamber photoreactor, to reduce the detrimental effects originating from the radiation intensity gradient within the irradiation chamber by intensely mixing the medium while it is present within the single chamber (French Patent Specification No. 1,560,780; German Offenlegungsschrift No. 1937126). However, even at very high turbulences an ideal mixture in which all particles of the medium would be exposed to the same mean radiation intensity cannot be attained. Still, not even such ideal mixture would be capable of removing the effect of the radiation intensity gradient within the medium since the mean radiation intensity will decrease with increasing depth. As will be shown by detailed calculation, the gradient will become effective, to a degree acceptable for practical purposes, at irradiation depths at which not more than 60%, and preferably 50%, of the incident radiation is absorbed. Thus the efficiency of purification or disinfection, respectively, will be considerably higher in a two-chamber photoreactor as compared to a single-chamber photoreactor of the same overall depth. A further advantage in the multiple chamber photoreactor arises from removal of the effect of the flow characteristics of the medium within the irradiation chambers on the purification or disinfection, respectively, under such conditions. Specific means for generating turbulent flow through the irradiation chamber, therefore, may be dispensed with in multiple chamber photoreactors.

To increase the degree of disinfection it may be advantageous to introduce an oxidizing agent into the medium before or during irradiation. The oxidizing agent may be oxygen, ozone, halogen, or some hypohalogenite, for example. Thus not only oxidative decomposition of impurities present in the medium will be furthered, but also the disinfection will be favorably influenced by additional secondary bactericidal effects.

Sensitivities of microorganisms towards ultraviolet radiation differ very much; for instance, that of fungi or algae is lower by two orders of magnitude than the sensitivity of bacteria. In the use of flow reactors for disinfection there will thus result a wide dosage range which may not be covered in its entirety simply by increasing the flux of radiation emitted from the radiation source and/or by reducing the throughput of the medium being irradiated. According to the invention it is therefore provided that at least a portion of the flow of the irradiated medium after passing the flow reactor is reintroduced into the same. Thus the medium being irradiated is fed a number of times through the reactor and will become irradiated with a corresponding multiple of the single passage dose. Such a procedure is also recommended in cases in which varying amounts of the disinfected medium are withdrawn from the ultraviolet disinfection unit.

According to the process of the invention the medium is exposed to ultraviolet radiation in the wavelength range between 260 and 280 nm. Ultraviolet radiation of this wavelength range is particularly effective in photodisinfection because microorganisms show maximum sensitivity in this range (L. J. Buttolph, "Practical Application and Source of Ultraviolet Energy"; Radiation Biology, McGraw Hill, New York 1955, Vol. 2, pages 41–93). Irradiation within that wavelength range also prevents photochemical formation of precipitates from media containing iron or manganese which precipitations occur on irradiation with low pressure mercury lamps at 254 nm. Another particular advantage of irradiating in the 260 to 280 nm wavelength range resides in the strong decrease in the absorption of iron or manganese containing impurities within this range which therefore act much less as a radiation filter diminishing the efficiency of the radiation in the photodisinfection than in the wavelength range as emitted by low pressure mercury lamps.

In accordance with the process of the invention the medium is advantageously passed successively through the irradiation chambers of the flow reactor. Thereby, as explained above, the efficiency of the purification or disinfection, respectively, will be considerably increased. the flow rates within each of the irradiation chambers of the multiple chamber flow reactor being increased over the flow rate in a single chamber photoreactor. Flow short-circuits occurring in single chamber photoreactors at high chamber depths and concurrent low flow rates will thus be avoided because of the increased flow rates at smaller cross-sections of the irradiation chamber. Such flow short-circuits will result in the formation of highly differentiated flow rates within the radiation field of the single chamber photoreactor and such differentiation will tend to become more pronounced at decreased flow rates and may result in the overall result of the irradiation being questionable. Additionally it is recommended to operate the multiple chamber photoreactor at a flow rate at or above the limit of turbulence of the medium flowing therethrough. Thus not only the formation of precipitates from the irradiated medium will be effectively suppressed in the mutliple chamber photoreactor but furthermore the heat transfer from the radiation source to the medium flowing through that chamber which is immediately adjacent to the radiation source will be particularly favorable so that overheating is avoided.

The considerable increase in the efficiency of the flow reactor by the described subdividing is not subject to the medium being fed successively through all of the irradiation chambers of the flow reactors. To a significant extent this increase is an intrinsic property of the multiple chamber photoreactor itself. To wit, if the medium is conducted in parallel through the irradiation chambers the flow rate in each single chamber may be adjusted such that the same minimum dose is applied in each of said irradiation chambers so that the same degrees of disinfection will be obtained and the portions of the medium flowing at different flow rates may be recombined after leaving the irradiation chambers. While parallel directions of flow are more elaborate with respect to apparatus and equipment, such may be advantageous if simultaneous irradiation of different media is desired.

The apparatus according to the invention is characterized by: the flow reactor is subdivided into separate irradiation chambers by windows extending normally with respect to the general direction of irradiation and made of material transparent for the ultraviolet radiation; the radiation incident into the medium present in the second irradiation chamber from the radiation source amounts to fractions of the radiation entering into the irradiation chamber next to said radiation source; and the monitoring equipment for maintaining the predetermined minimum irradiation dose comprises medium flow control means connected to the input or the outlet of said flow reactor. The fraction of the radiation incident in the second irradiation chamber from the radiation source should amount to at least 50% of the radiation entering into the irradiation chamber next to said radiation source and the absorption in the last said irradiation chamber should not exceed 50% with the total absorption in a flow reactor having up to 5 irradiation chambers not exceeding $(1-0.5^n)\cdot 100$ percent of the overall incident radiation, n representing the number of irradiation chambers.

In the field of hospital hygiene disinfection units are known which operate in such a way as to circulate the medium to be disinfected, like the wash water of air conditioners (of the type wherein there is direct contact between the air and water) through a tank into which a radiation source comprising one or more lamps is inserted in an immersion type arrangement with each lamp being fitted into an enveloping tube. Such arrangements have unfavorable flow conditions resulting in portions of the water in the tank receiving much higher radiation doses than required while the greater portion thereof will remain exposed to less than the required dose. Therefore, there is the danger that such water when contacting the air being conditioned will give off germs to that air. According to the present invention, the enveloping tube for each lamp is surrounded by at least one silica glass tube so as to form at least one inner irradiation chamber and that said inner irradiation chambers are connected in common either to the input or to the outlet of the flow reactor. Contrary to the known arrangements such apparatus ensures that the irradiation occurs at the minimum dose required independent of the direction of flow through the inner irradiation chambers. If the inner irradiation chambers are then connected to the input, irradiation in the presence of oxygen or other gases will be facilitated; if connected to the flow reactor outlet optimally disinfected water will be delivered at the spray nozzle of the air conditioner.

DESCRIPTION OF THE DRAWINGS

FIG. 1 is an isometric view of a first embodiment of the multichamber photoreactor according to the invention;

FIG. 2 is a longitudinal section through a component of a second embodiment of the multichamber photoreactor according to the invention;

FIG. 2A is a section corresponding to FIG. 2 illustrating a modification of the component of that Figure;

FIG. 3 is a perspective view of a detail of the embodiment of FIG. 2;

FIG. 4 is a longitudinal section of a further development of the embodiment of FIG. 2;

FIG. 4A is a section corresponding to FIG. 4 and shows a modification of the component of that Figure;

FIG. 5 is a perspective exploded view of a detail in FIG. 4;

FIG. 7 is a plan view of the further development of the multichamber photoreactor as shown in FIG. 6;

FIG. 8 is a sectional view of a detail of the embodiment of FIG. 7;

FIG. 13 is a schematic flow diagram illustrating recirculating operation of a multichamber photoreactor according to the invention;

FIG. 13A is a flow diagram illustrating a modification of the recirculating operation of FIG. 13;

FIG. 14 is a sectional view of a detail in the equipment for recirculation as illustrated in FIG. 13;

FIG. 16 is a longitudinal section of a modified embodiment of the multichamber photoreactor as in FIG. 11 but with parallel flow; and FIG. 17 is a longitudinal section of another modification of the multichamber photoreactor having parallel flow.

DESCRIPTION OF SPECIFIC EMBODIMENTS

Figure 6:
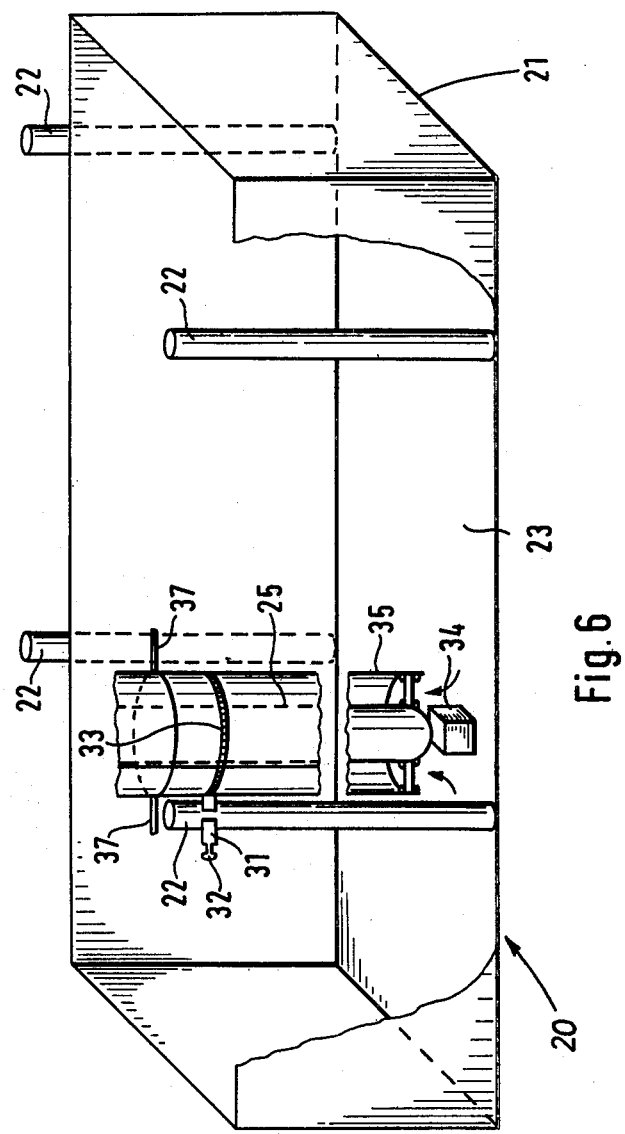
FIG. 6 is an isometric view, partially broken away, of the second embodiment of the multichamber photoreactor utilizing the component of FIG. 2.

The following disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

FIG. 1 illustrates a two-chamber photoreactor 1 including a trough-like container 2. A cover 3 is pivotably hinged to the container by hinges 4. A latch or the like, not shown, is employed to retain the cover in the closed position. Container 2 is made of metal like stainless steel. It also may be manufactured from any other ultraviolet resistant material meeting other requirements, as for instance food regulations (stoneware, enamel coated sheet metal, etc.). Secured to the inside of cover 3 are a series of paraboloidal reflectors arranged in parallel with respect to each other and provided with highly ultraviolet reflective surfaces. Ultraviolet lamps 6 are placed within the reflectors. The reflectors and lamps are normal with respect to the direction of flow of the fluid medium through container 2 in such a way that the flow cross-section of container 2, including the regions along the edges thereof, and uniformly irradiated. For disinfections water-cooled, antimony doped, high pressure xenon lamps will be employed; alternatively, low pressure mercury lamps of known design also may be used. For purification in the presence or in the absence of oxidizing agents, high pressure mercury lamps or other radiation sources of suitable emission ranges may be employed. The latch or cover is provided with a safety switch by means of which lamps 6 will become automatically switched off when the cover is opened.

Trough-like container 2 is subdivided along the direction of flow by a silica glass plate 7 to form two irradiation chambers 8, 9 with the plate forming a window, transparent to ultraviolet radiation, therebetween. Lower irradiation chamber 9 is limited to a fixed depth of 2 cm by the positioning of glass plate 7 while the depth of the medium in upper irradiation chamber 8 may be varied by means of level controller 17 subsequently described. Silica glass plate 7 is supported on a removable frame 10 made of stainless steel. The plate is sealingly secured to frame 10 which in turn is sealingly secured to the interior walls of container 2 by means of a cement resistant to ultraviolet radiation. Instead of by cement sealing may also be obtained with a preformed and ultraviolet-resistant gasket.

Irradiation chambers 8 and 9 communicate with each other at their respective ends remote from the input and outlet of trough-like container 2. Upper irradiation chamber 8 is connected to a flow rate limiter 12 via supply conduit 11. The flow rate limiter serves to limit the flow rate to a predetermined maximum admissible value independent of the prevailing input pressure (flow rate limiters of such kind are for instance sold by the Eaton Corporation, Controls Division, 191 East North Ave., Carol Stream, Ill. 60187). Supply conduit 11 opens into irradiation chamber 8 through perforated plate 13 constituting a balancing element to create a uniform flow pattern across the entire width of irradiation chamber 8. Irradiation chamber 9 opens into a discharge conduit 16 through a similar perforated plate 15 which also acts to balance the flow pattern. Discharge conduit 16 includes the level controller 17.

Perforated plates 13, 15 are made of material resistant to ultraviolet radiation and the medium flowing through the plates. Also, the plates should not give off detrimental contaminants to the medium passing therethrough. Such material may be stainless steel, coated metal, plastic, ceramic, quartz, glass. The width of the perforation will be such that flow-through will not be significantly impaired but that a uniform pattern of flow over the entire passage area is obtained. For achieving this purpose the perforation may be composed of circular holes, but other designs like slots, etc., will also be suitable. The perforated plates 13, 15 are sealingly cemented to the troughlike container 2 at one of their sides and to correspondingly formed transitional sections in supply conduit 11 and discharge conduit 16, respectively, at the other side.

Level controller 17 has an interior tube 19, which is sealingly and vertically movably guided in an open top vessel 20, and forms the outlet of troughlike container 2. This vessel has a protective cover 18 permeable to air made for instance of cotton to prevent the entry of impurities. By vertical adjustment of the interior tube 19 the depth of the medium in the flow reactor may be adjusted in upper irradiation chamber 8 in adaptation to the respective optical density of said medium.

Two-chamber photoreactor 1 comprises 20 low pressure mercury lamps (15 W, NN 15/44 Original Hanau Quarzlampen GmbH, Hanau, Federal Republic of Germany) positioned normally with respect to the direction of flow and equally spaced from each other over the length, 80 cm, of irradiation chambers 8, 9. Each lamp is placed in a reflector associated therewith. The smallest possible distance is maintained between adjacent lamp-reflector combinations. The total flux of ultraviolet radiation impinging on the surface of the medium (considering a maximum of 45% reflection losses and unavoidable losses in the edge regions) will then amount to about 60 watts (W) with a mean radiation intensity of $E = 25$ mW/cm$^2$. The following Table 1 shows a comparison of relevant data of two-chamber photoreactor 1 and of a single-chamber photoreactor of the same overall depth; Table 1 gives values of the flow rate Q-40 (m$^3$/h) at a minimum dose of 40 mWs/cm$^2$ for different transmission factors T (1 cm) of the medium and for different depths of upper irradiation chamber 8.

TABLE 1

Comparison of Two-Chamber Photoreactor 1 and a Single-Chamber Photoreactor of Equal Overall Depth, Flow Rates Q-40 at Minimum Dose of 40 mWs/cm$^2$

| T(1 cm) Q-40 depth d of | cm | 0.9 m$^3$/h | cm | 0.7 m$^3$/h | cm | 0.6 m$^3$/h | cm | 0.6 |
|---|---|---|---|---|---|---|---|---|
| upper chamber 8 | 4 | 14.7 | 2 | 4.94 | 2 | 3.89 | 1 | 3.24 |
| lower chamber 9 | 2 | 5.74 | 2 | 2.42 | 2 | 1.4 | 2 | 2.33 |
| Two-Chamber photoreactor | 6 | 20.44 | 4 | 7.36 | 4 | 5.29 | 3 | 5.57 |
| Single-Chamber photoreactor | 6 | 17.22 | 4 | 4.84 | 4 | 2.8 | 3 | 3.5 |
| Enhancement Factor F | | 1.18 | | 1.52 | | 1.89 | | 1.59 |

60 W ultraviolet radiation of 254 nm; 30 . 80 = 2400 cm$^2$ area of irradiation; mean radiation intensity E = 25 mW/cm$^2$. Effects of transmission factor T(1cm) and medium depth d in irradiation chambers.

It will be recognized from the foregoing Table 1 that the two-chamber photoreactor is suited for the range of transmission factors T(1 cm) from 0.95 to 0.5; at T(1 cm)$\geq$0.95 the depth of the medium in upper irradiation chamber 8 should be equal to or greater than 4 cm, at T(1 cm)$\leq$0.6 about 1 cm.

In the range of low transmission factors the depth in lower irradiation chamber 9 also should be reduced, for instance to 1 cm at T(1 cm)=0.4. In the latter case and under the conditions as given in the table with a depth of 1 cm in each one of the two chambers Q-40 will become 3.02 m$^3$/h and the enhancement factor will be 1.75. With a depth of 1 cm in lower irradiation chamber 9 two-chamber photoreactor 1 will be optimally adaptable to the range of transmission factors occurring in sewage disinfection. Losses of the effective ultraviolet radiation due to the use of reflectors will be more than compensated for by subdividing the photoreactor in accordance with the invention, whereby a more favorable result in terms of result for the energy input is achieved as compared to a single-chamber photoreactor. Two-chamber photoreactors of this kind may also be utilized in seawater disinfection.

The container 2 of photoreactor 1 may be constructed with two of the exterior walls thereof made of silica glass. In that event the radiation source may be placed outside those two walls in juxtaposition thereto. The lamps forming the radiation source are arranged pairwisely opposing each other in a system of single reflectors. By superposition of the radiation fields a substantial increase and a different spatial distribution of the interior radiation intensity is achieved which enables the minimum dose rate to be increased by more than 200 percent if irradiation depth and transmission factors are properly adapted to each other. In a photoreactor of an overall depth of 4.5 cm the dose rate delivered to a medium having a transmission factor of T(1 cm)=0.6 will be tripled if irradiated from both sides as compared to unilateral irradiation at the same dose rate.

FIGS. 2 to 8 show the design of a multichamber photoreactor with the radiation source in an immersion type arrangement.

In the longitudinal section of FIG. 2 a first embodiment of a component of the multichamber photoreactor is shown. It comprises a lamp 24 housed in an envelope tube 25 made of silicon glass which itself is introduced into a partitioning tube 35 also made of silica glass. For disinfection, lamp 24 is an antimony doped high pressure xenon lamp. Alternatively low pressure mercury lamps of known design may also be employed. For purifications in the presence or absence of oxidizing agents high pressure mercury lamps or other lamps emitting in suitable regions of wavelength may be utilized. Lamp 24 rests on a support 27 at the lower end of envelope tube 25. This support may be made of glass wool, for example. Near their upper ends envelope tube 25 and partitioning tube 35 are interconnected by means of ground glass joints 26, 36 which are held in sealing engagement by suitable, and conventional, retaining elements (such as sold by Schott & Gen., Mainz, Federal Republic of Germany). Two diametrically opposed connections 37 are carried by partitioning tube 35 below ground glass joint 36. At the lower end of the component as shown in FIG. 2 spacer means are provided to hold envelope tube 25 and partitioning tube 35 at equal distances from each other throughout their length. Said spacer means comprise two spring rings 29 concentrically arranged and interconnected by three resilient bars 30 spaced by an angle of 120° from each other (see FIG. 3). Spring rings 29 are retained intermediate small projections 28, 38 on the external wall of envelope tube 25 and the internal wall of partitioning tube 35, respectively. The projections are spaced angularly by approximately 120° at an axial distance adapted to the corresponding dimension of spring ring 29. Said spacer means may additionally be provided with a perforated plate to adjust a uniform flow pattern across the passage area as will be explained with reference to FIG. 5.

FIG. 4 illustrates a modified component similar to the one shown in FIG. 2. A lamp 24 of the kind as described above is located within an envelope tube 45 made of silica glass. Envelope tube 45 is surrounded by a partitioning tube 55 made of silica glass and tapered to form an upper end of smaller diameter just slightly larger than envelope tube 45. Two diametrically opposed connections 57 are provided adjacent the narrower upper end of the partitioning tube. Envelope tube 45 and partitioning tube 55 are concentric with respect to each other. They are sealingly interconnected at their upper ends by an overlapping sealing collar 46 made of an elastic plastic material resistant to ultraviolet radiation and to the medium flowing through. Sealing collar 46 is secured by means of clamps 48. Spacer means 67 are provided at the lower end of the multichamber photoreactor component to hold envelope tube 45 and partitioning tube 55 at equal distances from each other throughout their length. Corresponding to the FIG. 2 structure the spacer means 67 are disposed intermediate projections 28 formed on envelope tube 45 and projections 68 formed on partitioning tube 55. The spacer means (see FIG. 5) comprises two spring rings 29 interconnected by resilient bars 30. The exterior one of spring rings 29 carries holders 69 projecting axially upwardly from the periphery thereof. The ends 70 of the holders 69 are bent radially inwardly to hold a plate 71 which rests on spring ring 29. Passage openings 72 in plate 71 are uniformly distributed across the passage area; they are associated with the irradiation chamber 49 as defined by envelope tube 45 and partitioning tube 55. Plate 71 is made of a material resistant to ultraviolet radiation and the medium flowing through. Also, plate 71 will not give off detrimental contaminants to the medium passing therethrough. Such material may be one of the following: stainless steel, coated metal, plastic, ceramic, glass, silica. Passage openings 72 are of circular or other suitable cross-section and sufficiently wide to not impair the through-flow substantially, but sufficiently small to generate a uniform flow pattern across the area of passage. The entire engagement is such that each of holders 69 will be positioned intermediate the projections 68 at the interior wall of partitioning tube 55.

A number of modifications can be introduced into the embodiments as described hereinbefore. In the modification as shown in FIG. 2A the open end of the partitioning tube 35A is fused, at 36A, to the envelope tube 25A to form a unitary component. However, such construction is expensive to manufacture and sensitive to handle. In a more simple design the spacer means may be just formed by plate 71 (FIG. 5) with passage openings 72; the upper ring of projections 28, 68 may then be eliminated, plate 71 being held in abutment to the lower ring of said projections by a suitable snap ring.

As illustrated in FIG. 4A, the FIG. 4 component may be modified to have an additional silica glass tube 52. This additional tube is concentric with respect to silica glass tubes 45 and 55. Silica glass tube 52 is closed at its lower end. Its open end is tapered and is sealingly connected to silica glass tube 55 by means of an overlapping sealing collar 51 secured by clamps 50, similar to the way partitioning tube 55 is sealingly connected to envelope tube 45. The upper, tapered end of silica glass tube 52 is secured to partitioning tube 55 closely adjacent to connections 57. In the wall of silica glass tube 52 there are at least two passage openings 53 which are located close to the tapered end and which are spaced uniformly about the circumference of silica glass tube 52.

Partitioning tube 55 is extended towards a retainer engaging the interior bottom of silica glass tube 52. That retainer comprises a ring 59 from which a number of spring blades 60 project to receive and hold the respective end of partitioning tube 55. There is sufficient space between the edge of partitioning tube 55 and ring 59 as well as between spring blades 60 to permit an uninhibited flow between the irradiation chambers separated by partitioning tube 55. Alternatively, the edge of partitioning tube 55 may abut the face of ring 59, with suitable cut-outs provided in the edge of partitioning tube 55 to allow communication between said chambers. Ring 59 and spring blades 60 are made of a material resistant to ultraviolet radiation and the through-flowing medium; also, said members will not give off any detrimental contaminants to the medium passing therethrough (such material may be either of the following:

stainless steel, coated metal, preferably coated with a fluorinated hydrocarbon polymer).

Any one of the components represented in FIGS. 2, 2A, 4 and 4A, including lamp 24 together with a tank 21, form the flow reactor, generally 20, of a two-chamber photoreactor (FIG. 6). Support bars 22 are carried by the longitudinal walls of tank 21. A component such as shown in FIGS. 2, 2A, 4 or 4A is attached to each of support bars 22 respectively. Only one of such components is shown in FIG. 6. Tank 21 and support bars 22 are made of stainless steel and welded to each other. They may also consist of different materials suitably connected with each other. Tank 21 should be manufactured from ultraviolet resistant material satisfying all other requirements like for instance food regulations. The tank 21 is open at the top and has a discharge conduit (not shown) which forms the source of the irradiated (purified) medium.

In the combination of the component as shown in FIG. 4A with tank 21 the discharge is conveniently formed by an overflow tube extending from the bottom of tank 21 to the level of passage openings 53. Thereby, the desired constant depth of charge in tank 21 is maintained.

The component is secured to support bar 22 by any suitable means. As shown, a fastener bushing 31 including a set screw 32 is used. The bushing carries a chain 33 which may have a protective cover, if desired, and which encircles said component to be secured to bushing 31. Retaining means of this kind in connection with irradiation devices are known and available commercially so that no detailed description thereof is warranted here. At the bottom of tank 21 there are supports 34 on which the respective component will rest to add to its safer mounting.

In operation of flow reactor 41 connections 37 or 57, respectively, of the component as shown in FIGS. 2 and 4 are interconnected to a common discharge (not shown, but similar to 90 in FIG. 7) which is at a level below the top of the tank. The medium entering tank 21 through the intake conduit (similar to 91 in FIG. 7) will at first flow through the tank (which forms the first irradiation chamber 23) and then will pass through the inner radiation chamber 39 or 49, respectively, entering the open lower end thereof. From the inner irradiation chambers the medium discharges through the discharge conduit. The partitioning tubes 35, 55 form windows, transparent to ultraviolet radiation, through which the ultraviolet radiation not absorbed in the inner chambers 39, 49 may escape into the medium in the tank.

FIGS. 7 and 8 show another embodiment of a flow reactor, generally 40. It is similar to the two-chamber photoreactor 20 shown in FIG. 6. Tank 21 carries a supply connection 91 and is closed by a cover 80 provided with openings 81. A component as shown in FIGS. 2, 2A, 4 or 4A extends through each opening with the openings then being sealed by a retaining means, generally 82. Each retaining means 82 comprises a collar 83 projecting upwardly from cover 80 and guiding the respective exterior silica glass tube 35, 55. The silica glass tube carries an O-ring 84 engaging a chamfered surface 85 formed at the interior edge of the upper end of collar 83. The O-ring 84 is sealingly secured in its position by a compression ring 88 retained by means of screws 86 engaging threaded bores 87 in the top surface of collar 83. Connections 37 of a component as shown in FIG. 2 are connected to a common discharge line 90 via connecting conduits 89. In corresponding manner the components as shown in FIG. 4 or other components as described above may be sealingly retained an cover 80.

The open-top multichamber photoreactor as illustrated in FIG. 6 is advantageously employed in connection with air conditioning units the discharge of which is located immediately above tank 21; the closed arrangement as illustrated in FIG. 7 enables other applications in which the medium is intended to be irradiated in relatively pressure-free circulation. To ensure that no less than the required minimum dose is applied it will be expedient to incorporate a flow rate limiter into the supply conduit. The disadvantage of the inhomogeneity in the distribution of the radiation intensity through the first irradiation chamber 23 as formed by tank 21 in such multichamber photoreactors is compensated for by conducting the medium through the interior chamber 39 or 49, respectively, in which the medium will be exposed to a high minimum radiation intensity at a lower gradient thereof under well-defined conditions. Depending upon respective requirements, a smaller or greater number of the components as shown in FIGS. 2 or 4 may be utilized in multichamber photoreactor 20 or 40, respectively. The direction of flow therethrough will not be decisive in their operation. If high degrees of disinfection are required it will be expedient to have the medium finally pass through the interior irradiation chamber 39 or 49, respectively. In case that a gas, for instance oxygen, is to be introduced into the medium during irradiation the reverse direction of flow is recommended.

For the purification (particularly for sterilization or disinfection) of media, which are intended to be conducted at high output through a flow reactor equipped with an ultraviolet radiation source emitting predominantly in the range between 240 and 320 nm, such apparatus will be specifically suited as having the flow reactor and the radiation source arranged annularly with respect to each other. Thus an annular flow reactor may surround a radiation source placed in the interior space thereof. Also, an external radiation source comprising a series of lamps each placed in a respectively associated reflector with the reflectors encircling the flow reactor, even both kinds of radiation sources, may be provided. The flow reactor may also be of tubular design and, then, is combined with an external radiation source. The following Table 2 will show with reference to an annular flow reactor having an interior diameter $D_i=4$ cm and varying outer diameters $D_a=6$ to 14 cm the decrease in the inner radiation intensity E on radial irradiation of a medium having the transmission factor $T(1\ cm)=0.6$. In case of a low pressure mercury lamp placed in axial position within the interior space of said flow reactor and having an effective axial length of 1 m, the emission in radial direction along said length will yield an irradiation intensity of 15 W ultraviolet at 254 nm at the interior face of the flow reactor passing through the same and entering the medium. With the effective interior irradiated surface being $\pi \cdot D_i \cdot 100$ cm$^2$=1256.6 cm$^2$, the mean radiation intensity at this surface will be $E_i=11.94$ mW/cm$^2$. The Column 2 in Table 2 will show diameters D and depths of irradiation d in cm, associated geometry factors G, transmissions T as well as the product $G \cdot T = E_{rel}$ to indicate relative radiation intensities at respective depths; column $E_d$ shows interior radiation intensities at different depths; column $V_d$ indicates respective annular chamber volumes. The last column of Table 2 presents respective throughputs Q-40 in m³/h at an observed minimum irradiation dose of 40 mWs/cm² calculated with the assumption of uniform flow.

TABLE 2

Radiation Intensities $E_d$ and Throughputs Q-40 of an Annular Single-Chamber Photoreactor at Various Irradiation Depths d

| D cm | d cm | G | T | $E_{rel(d)}$ G . T | $E_d$ mW/cm² | $V_d$ ml | Q-40 m³/h |
|---|---|---|---|---|---|---|---|
| 4 | 0 | 1.0 | 1.0 | 1.0 | 11.94 | 0 | 0 |
| 6 | 1 | 0.666 | 0.6 | 0.399 | 4.76 | 1571 | 0.67 |
| 8 | 2 | 0.5 | 0.36 | 0.18 | 2.15 | 3770 | 0.73 |
| 10 | 3 | 0.4 | 0.216 | 0.086 | 1.03 | 6597 | 0.61 |
| 12 | 4 | 0.333 | 0.126 | 0.042 | 0.53 | 10053 | 0.47 |
| 14 | 5 | 0.286 | 0.078 | 0.022 | 0.26 | 14137 | 0.33 |

15 W ultraviolet radiation of 254 nm over 1 m in axial position; envelope tube $D_i$ = 4 cm.

As will be seen from Table 2, the inner radiation intensity $E_d$ strongly decreases with increasing depth d, while the annular chamber volume considerably increases contrary thereto. With a medium to be irradiated having a transmission factor of T(1 cm)=0.6, Q-40 will become 0.73 m³/h at the maximum at a depth of d=2 cm (see Table 2). At greater depths Q-40 will decrease since the influence of the larger annular chamber volumes which are exposed to only small inner radiation intensities $E_d$ will become predominant. The maxima of throughput Q-40 achievable with media having different transmission factors will be found at different depths d: with T(1 cm)=0.7, Q-40(max)=1.32 m³/h at d=2 cm; with T(1 cm)=0.8, Q-40(max) will be 1.95 m³/h at d=4 cm; with T(1 cm)=0.9, Q-40(max) is 3.42 m³/h at d=5 cm. If the depth of the single-chamber photoreactor remains constantly d=5 cm, the maximum attainable throughputs Q-40 will be 2.56; 1.42; 0.73 m³/h with T(1 cm)=0.9, 0.8, 0.7, respectively.

The following Table 3 will show the situation in the case of a medium again with T(1 cm)=0.6 and of a multichamber photoreactor having the same dimensions and subdivided into irradiation chambers of 1 cm depth each by ultraviolet transparent partitions (having negligible dimensions). The first 6 columns in Table 3 include the same data as Table 1. Into column $V_k$ the volumes of each one of the respective irradiation chambers have been entered, while column Q-40(k) lists the throughputs for each of said irradiation chambers at a minimum irradiation dose of 40 mWs/cm². The last column in Table 3 lists the irradiation doses E·t(k) in mWs/cm² applied to the medium in each respective irradiation chamber if passed through all said chambers consecutively at a flow rate of 1.61 m³/h.

TABLE 3

Radiation Intensities $E_d$ and Throughputs Q-40 of an Annular Multichamber Photoreactor subdivided into 5 Chambers of 1 cm Depth each

| D cm | d cm | G | T | $E_{rel}$ G . T | $E_d$ mW/ cm² | $V_k$ ml | Q-40(k) m³/h | E . t(k) at Q = 1.61 m³/h mWs/cm² |
|---|---|---|---|---|---|---|---|---|
| 4 | 0 | 1.0 | 1.0 | 1.0 | 11.94 | 0 | 0 | — |
| 6 | 1 | 0.666 | 0.6 | 0.399 | 4.76 | 1571 | 0.67 | 16.72 |
| 8 | 2 | 0.5 | 0.36 | 0.18 | 2.15 | 2199 | 0.425 | 10.57 |
| 10 | 3 | 0.4 | 0.216 | 0.086 | 1.03 | 2827 | 0.26 | 6.51 |
| 12 | 4 | 0.333 | 0.126 | 0.042 | 0.53 | 3456 | 0.16 | 4.09 |
| 14 | 5 | 0.286 | 0.078 | 0.022 | 0.26 | 4084 | 0.097 | 2.37 |
|   |   |   |   |   |   |   | 1.61 | 40.27 |

15 W ultraviolet radiation of 254 nm over 1 m in axial position; envelope tube $D_i$ = 4 cm.

As will result from inspecting the last column in Table 3, a total throughput of Q-40=1.61 m³/h is feasible if the irradiation chambers are passed in parallel with the observation of a minimum irradiation dose of 40 mWs/cm² in each single chamber. Consequently, it will follow from this column that the medium will have been irradiated at a total irradiation dose of 40 mWs/cm² if passed through the series-connected irradiation chambers at a flow rate of 1.61 m³/h. For media having transmission factors of T(1 cm)=0.7, 0.8, and 0.9, respectively, the corresponding overall values of Q-40 are 2.28, 3.15 and 4.37 m³/h, respectively.

In summary, the foregoing discussion with reference to Tables 2 and 3 shows that subdivision of the photoreactor will result in a considerable output increase. The results are compiled in Table 4. The lines therein show throughputs Q-40(max) at optimum respective depths and throughputs Q-40 at depths of d=5 cm for different transmission factors T(1 cm)=0.6–0.9 for single-chamber photoreactors corresponding to Table 2, the overall throughputs Q-40 of a multichamber photoreactor comprising 5 irradiation chambers each having a depth of 1 cm (overall depth d=5 cm), as well as the enhancement factor F giving the increase in the throughput of the multichamber photoreactor over the throughput of the single-chamber photoreactor.

TABLE 4

Comparison of Throughputs of Single and Multichamber Photoreactors for Media having Various Transmission Factors

|  | T(1 cm) | 0.9 | 0.8 | 0.7 | 0.6 |
|---|---|---|---|---|---|
| Q-40 (max) | m³/h | 2.56 | 1.46 | 0.99 | 0.73 |
| Q-40 | m³/h | 2.56 | 1.42 | 0.73 | 0.33 |
| Q-40 (total) | m³/h | 4.37 | 3.15 | 2.28 | 1.61 |
| F |  | 1.70 | 2.16 | 3.13 | 4.88 |

From Table 4 the advantages of the multichamber photoreactor over the single-chamber photoreactors of known design will become immediately evident. Thus without any additional radiation source or any other measures the output may be increased by more than 100% just by subdividing the one irradiation chamber as described to form the multichamber photoreactor. Thus the subdivision of a single-chamber photoreactor to form a multichamber photoreactor enables the throughput to be doubled without changing the applied radiation dose or, alternatively, the applied radiation dose to be doubled with the throughput remaining unchanged. Effects of such nature cannot be achieved by any kind of combination of single-chamber photoreactors. The increases in output achieved are the same in the examples discussed whether the irradiation chambers are connected in parallel or in series with respect to flow direction. In practice, however, series connection will have significant additional advantages. Thus the series connection will offer substantially higher safety with respect to flow short-circuits and in addition essentially improved mixing of the medium to be irradiated within the entire radiation field. Actually, in series connection of the irradiation chambers the flowing medium is conducted through the irradiation zone in alternating directions of flow, the positive reversal of the layers in the flowing medium enforcing reorientation of the fluid particles during their passage through the irradiation chambers. Furthermore, in series connection the interior irradiation chambers in particular are operated at relatively high rates of flow, the through-flow will occur at substantially higher Reynold's numbers as compared to single-chamber photoreactors. In addition to better mixing this will favorably affect suppression of the formation of precipitates.

More specifically, Table 4 also demonstrates that the enhancement factor F strongly increases with decreasing transmission factors at constant overall depth. This will follow from the single-chamber photoreactor having an optimum chamber depth for each respective transmission factor, i.e., such photoreactors are only adaptable to a minor extent to media having variable or different transmission factors. In contrast multichamber photoreactors are of great advantage in that their outputs will be more favorable even if used for media having highly variable or different transmission factors. In the case of a medium having low transmission, the result of the irradiation in the multichamber photoreactor will not be impaired by considerable proportions of the overall depth receiving merely very low irradiation doses; while, on the other hand, in the case of media having high transmission the multichamber photoreactor will permit higher utilization of the given radiation flux by means of the high overall depth of all irradiation chambers combined.

Multichamber photoreactors with annular respective arrangements of radiation source and flow reactor are constructed from a number of silica tube sections which are placed inside each other according to their increasing diameters with the diameters selected so as to enable coaxial irradiation chambers of the respectively desired depths to be formed. Such silica glass tubes can be manufactured to the required precision in their dimensions and are commercially available with appropriate diameters and wall thicknesses. The silica glass tubes are centered relative to each other and then retained by closure members closing the flow reactor at the end faces thereof (see further below). The closure members have grooves sealable for instance by packing glands within which the silica glass tubes are retained. They are provided with internal passages and connections for effecting supply and discharge of the medium in parallel or series connection of the irradiation chambers. FIGS. 9 to 12 will show specific embodiments of annular multichamber photoreactors having an interior radiation source, pressure balancing equipment, and an exterior radiation source, respectively.

Figure 9:
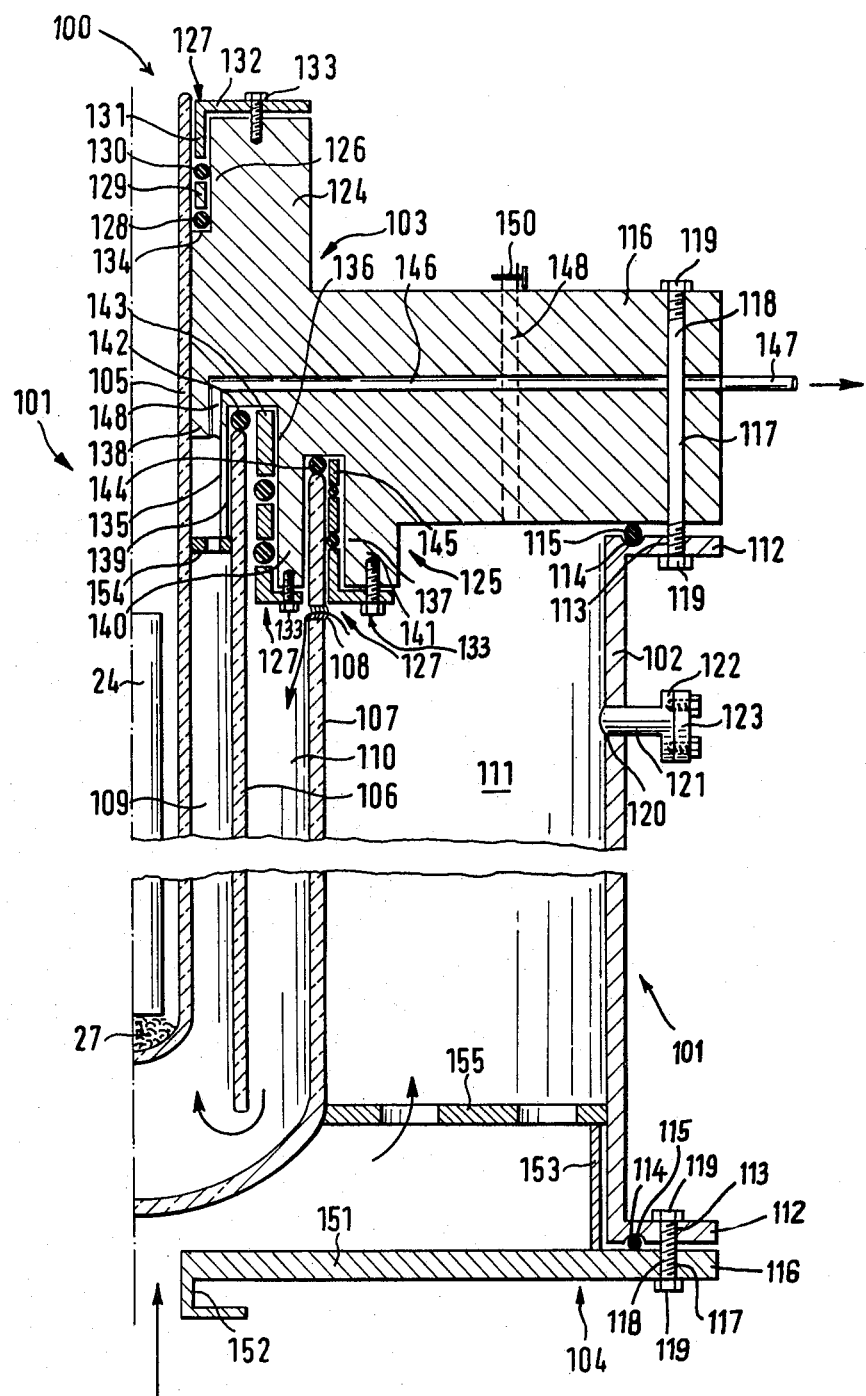
FIG. 9 is a longitudinal section of a portion of a third embodiment of the multichamber photoreactor according to the invention.

One half of a three-chamber photoreactor 100 designed for irradiation from its interior is illustrated in longitudinal section in FIG. 9. A lamp 24 of the aforementioned kind is included therein and may be singly or multiply reversed on itself to obtain increased radiation intensity. Lamp 24 is disposed in the interior of a flow reactor 101 near the axis thereof. The flow reactor includes a housing formed by an exterior casing 102 opaque to the radiation, a first closure member, generally 103, and a second closure member, generally 104. Within the housing is an interior, intermediate tube 105 transparent to the radiation and held by first closure member 103. Interior envelope tube 105 is a silica glass tube closed at one end at which end lamp 24 rests on a glass wool packing 27. Flow reactor 101 is subdivided into three irradiation chambers 109, 110, 111 by silica glass tubes 106 and 107. Tubes 106 and 107 form windows through which the ultraviolet radiation may pass. Silica glass tube 107 is closed at one end and provided with passage openings 108 in the wall near its open end. Both tubes 106 and 107 are held by first closure member 103.

Exterior casing 102 is provided with annular flanges 112 having bores 113 spaced adjacent their periphery for connection to closure members 103, 104 at the respective ends. The end faces of annular flanges 113 have recesses 114 to receive sealing O-rings 115. Closure member 103, 104 include flanges 116 having bores 117 spaced adjacent their periphery corresponding in number and diameter to bores 113 in annular flanges 112. Exterior casing 102 and closure members 103, 104 are arranged with their annular flanges 112 and 116 such that bores 113 and 117 are aligned to each other so that said members can become firmly interconnected by threaded bolts 118 extending through bores 113 and 117 and by nuts 119.

For purposes of observation and monitoring exterior casing 102 has an observation port in the region of the field of radiation emitted by lamp 24 and formed by an opening 120 into which a tube 121 having an outer annular flange 122 is secured. During non-use tube 121 is closed by a cover 123 firmly and sealingly, for instance by screwing, connected to annular flange 122. During use tube 121 is connected through a silica window (which may be cover 123) to the photodetector of an equipment for monitoring the radiation passing through the entire depth of flow reactor 101. To utilize the ultraviolet output impinging on the interior wall of exterior casing 102 in the irradiation of media having high transmission said interior wall may be provided with material reflective for ultraviolet rays. If an exterior casing of silica glass is employed, the reflective surface may also be located on the exterior wall of the casing to avoid the reflectivity to become affected by the medium.

Exterior casing 102 and closure members 103, 104 are made of metal like stainless steel, of metals having a protective coating like glass, enamel, plastic, or zinced iron sheet material, of ceramic; or any material having the appropriate mechanical strength which is resistant against ultraviolet radiation and does not give off foreign matter or noxious contaminants to the medium flowing therethrough will be applicable. To increase the mechanical strength and to facilitate processing and handling of envelope tube 105 and silica tubes 106, 107 said tubes may be fused to extensions for instance of vitreous silica positioned outside the radiation field as emitted by lamp 24.

Closure member 103 is generally of annular configuration and has an internal diameter closely adapted to the external diameter of envelope tube 105. The annular closure member 103 has two axial portions 124, 125 each projecting from a face of flange 116 and serving to retain envelope tube 105 and silica glass tubes 106, 107. First portion 124 is provided with a counterbore 125 at its outer end into which a packing gland 127 is inserted. Packing gland 127 comprises two O-rings 128, 130 separated by a guiding bush 129 and pressed against a step 134 formed at the interior end of counterbore 126 by means of a compression sleeve 131. Sleeve 131 includes an annular flange 132 which is secured to the outer face of first axial portion 124 by screws 133. Thus envelope tube 105 will be firmly and sealingly retained at the first axial portion 124. Second axial portion 125 is provided with three concentric annular grooves 135, 136, 137 each extending axially from the inside of flow reactor 101 and their depth decreasing radially from the interior to the exterior and separated by annular webs 138, 139, 140 and 141. Webs 138 and 139 have small and different axial heights and define the radially innermost annular groove 135 of greater depth. Radially intermediate annular groove 136 is defined by web 139 and web 140 of greater axial height while radially outermost annular groove 137 of smallest depth is enclosed between two webs 140, 141 of equal axial heights. Intermediate annular groove 136 serves to accommodate a first end of silica glass tube 106 which abuts the base of annular groove 136 with the interposition of an O-ring 142, a bushing 143 enclosing O-ring 142 and said first end of silica glass tube 106. Tube 106 is retained firmly and sealingly within intermediate annular groove 136 by a packing gland 127 secured to the outer face of web 140 by screws. The outermost annular groove 137 serves to accommodate silica glass tube 107 closed at one end. The open end of tube 107 abuts the base of annular groove 137 with the interposition of an O-ring 144. A bushing 145 encloses O-ring 144 and said open end of silica glass tube 107. Tube 107 is firmly and sealingly retained within outermost annular groove 137 above passage openings 108 by a packing gland 127 secured to the outer face of web 141 by screws.

Closure member 103 has two radial passages 146 ending at diametrically opposed positions in connections for conduits 147 at the circumferential surface of flange 116. Both radial passages 146 are connected each at the interior end with a respective axial passage 147 opening into the base of annular groove 135. Thus communication is provided between conduits 147 and the internal irradiation chamber 109. Additionally, flange 116 has a vent passage 148 extending axially therethrough and connecting the exterior irradiation chamber 111 to a venting valve 150 located at the outer face of flange 116.

Closure member 104 comprises a plate 151 having a central connection 152. A ring 153 is engaged to the interior face of plate 151 and peripherally abuts the interior wall of exterior casing 102.

Flow is conducted through three-chamber photoreactor 100 between connections 147 and 152 through irradiation chambers 109, 110, and 111. Irradiation chambers 110 and 111 communicate with each other through the passage openings 108 in the wall of silica glass tube 107 closed at one end. To generate a uniform flow pattern annular perforated plates 154, 155 are provided. Perforated plate 154 is secured to web 139 of first closure member 103 and affects the flow passing through interior irradiation chamber 109. Perforated plate 155 engages ring 153 which engages the interior face of plate 151 of second closure member 104 and affects the flow passing through exterior irradiation chamber 111. Silica glass tube 107 abuts the interior edge of plate 155 and thus is additionally guided at the closed end thereof. Perforated plates 154, 155 are made of a material resistant to ultraviolet radiation and to the medium flowing therethrough and which does not give off any foreign matter or noxious contaminants to the medium. Such material might be stainless steel, coated metal, plastic, ceramic, silica, or glass. The width of the perforation is such as to not substantially impair the flow but to generate uniform flow pattern across the passage area. For that purpose the holes forming the perforation may be substituted with appropriate, differently shaped openings.

For continuous operation the direction of flow through flow reactor 101 is hardly significant. Substantial differences, however, may exist at the start of the operation. With repeatedly interrupted operation it may be desirable to obtain a medium of the required degree of purification or disinfection even within very short periods of time after start. In that case it will be expedient to have the medium flow from connection 152 and the exterior irradiation chamber 111 through the interior irradiation chamber 109 to connections 147. With the same direction of flow it will be achieved in cases of deposit formation that interfering effects are restricted to the exterior irradiation chambers without rapidly calling the entire result into question. For the reason of lamp cooling, and also in cases in which gases are introduced, a direction of flow from the interior to the exterior will be preferred in general.

A preferred embodiment of the three-chamber photoreactor 101 as illustrated in FIG. 9 has an interior irradiation chamber 109 with a depth of 0.8 cm (measured radially), an intermediate irradiation chamber 110 with a depth of 1 cm, and an exterior irradiation chamber 111 with a depth of 3.4 cm. The external diameter of envelope tube 105 is 4 cm, the wall thickness of silica glass tubes 106, 107 is 0.4 cm each, and the transmission of silica glass at 254 nm of such thickness is $T(0.4 \text{ cm}) = 0.92$. Within envelope tube 105 there is placed a low pressure mercury lamp (G 36 T 6; General Electric) having an effective arc length of 75 cm, the flux of radiation over such length supplying 11 W of 254 nm ultraviolet radiation power to the medium at the irradiated inner wall of envelope tube 105. For purposes of better comparison the numbers given in the following Table 5 are normalized to a radiation flux of 15 W ultraviolet radiation at 254 nm over an effective length of 1 m of the irradiated wall of irradiation chamber 109. Table 5 will show in analogy with foregoing Table 4 values for the throughput Q-40 ($m^3/h$) of three-chamber photoreactor 101 having an overall depth (measured radially) of $d = 5.2$ cm and of single-chamber photoreactors having depths of $d = 1$ cm and $d = 5.2$ cm, respectively, for media of different transmission factors $T(1 \text{ cm}) = 0.1$ to $0.9$, as well as enhancement factors F in the throughput Q-40 of three-chamber photoreactor 101 as compared to that of the aforementioned single-chamber photoreactors.

TABLE 5

Comparison of Throughputs of Three-Chamber Photoreactor 100 and Single-Chamber Photoreactors having Depths of 1 and 5.2 cm, respectively, for Media of Various Transmission Factors

| T (1 cm) | | 0.9 | 0.8 | 0.7 | 0.6 | 0.5 | 0.4 | 0.3 | 0.2 | 0.1 |
|---|---|---|---|---|---|---|---|---|---|---|
| Q-40 Three-Ch. | $m^3/h$ | 3.53 | 2.46 | 1.75 | 1.26 | 0.93 | 0.49 | 0.48 | 0.32 | 0.16 |
| Q-40 Single-Ch. (d = 1 cm) | $m^3/h$ | 1.00 | 0.89 | 0.78 | 0.67 | 0.56 | 0.44 | 0.33 | 0.22 | 0.11 |
| Q-40 Single-Ch. (d = 5.2 cm) | $m^3/h$ | 2.59 | 1.40 | 0.70 | 0.31 | 0.12 | 0.04 | 0.01 | $2.10^{-3}$ | $2.10^{-}$ |
| F (d = 1 cm) | | 3.52 | 2.76 | 2.24 | 1.89 | 1.67 | 1.11 | 1.43 | 1.43 | 1.43 |

TABLE 5-continued

Comparison of Throughputs of Three-Chamber Photoreactor 100
and Single-Chamber Photoreactors having Depths of 1 and
5.2 cm, respectively, for Media of Various Transmission Factors

| T (1 cm)    | 0.9  | 0.8  | 0.7  | 0.6  | 0.5  | 0.4   | 0.3   | 0.2 | 0.1 |
|-------------|------|------|------|------|------|-------|-------|-----|-----|
| F (d = 5.2 cm) | 1.36 | 1.75 | 2.50 | 4.01 | 7.63 | 12.80 | 57.30 |     |     |

15 W UV radiation of 254 nm in axial position; envelope tube $D_i = 4$ cm.

As will follow from Table 5, the output of the single-chamber photoreactor having a depth of 5.2 cm provides for a throughput of Q-40=0.78 m³/h for a medium with T(1 cm)=0.7; with an outer diameter of the envelope tube of 4 cm and for a medium having the same transmission factor the throughput of the single-chamber photoreactor will have a maximum of Q-40(max)=1 m³/h at a depth of 2 cm. Triple subdivision as in three-chamber photoreactor 101 illustrated in FIG. 9 will yield a throughput of Q-40=1.75 m³/h, the enhancement factor even in comparison with the single-chamber photoreactor of optimum efficiency still amounting to F=1.75. Such a result is obtained although portions of the ultraviolet radiation emitted from the radiation source are absorbed by the silica glass of which silica tubes 106 and 107 consist (accounted for in the calculation).

Preferably, three-chamber photoreactors 101 of the type as illustrated in FIG. 9 will be utilized in all those cases in which high degrees of disinfection are attained for media with relatively low transmission factors, the use thus not being restricted to the disinfection of potable water and the like.

As shown in Table 5, single-chamber photoreactors will only be compatible with varying transmission factors in the range of T(1 cm)=0.9 to 0.3 if small depths as d=1 cm prevail, however, only at an expense in throughput. The decrease in output of the single-chamber photoreactor at depths in the range of d=5 cm already at T(1 cm)=0.7 will assume such considerable extent that very often media with smaller transmission factors cannot become disinfected economically. Instead, three-chamber photoreactor 101 as described with reference to FIG. 9 will have superior output and compatibility with varying transmission factors in the range of T(1 cm)=0.9 to 0.1. A three-chamber photoreactor 101 may be utilized in the entire field of disinfection of potable water, but will also be applicable to other media having transmission factors of T(1 cm)=0.6 to 0.25 like biologically pretreated sewage and also like sugar solutions, colorless vinegar and light wines. Also, a three-chamber photoreactor 101 in accordance with FIG. 9 will be useful for more specific purposes like water purification at high radiation doses.

Figure 10:
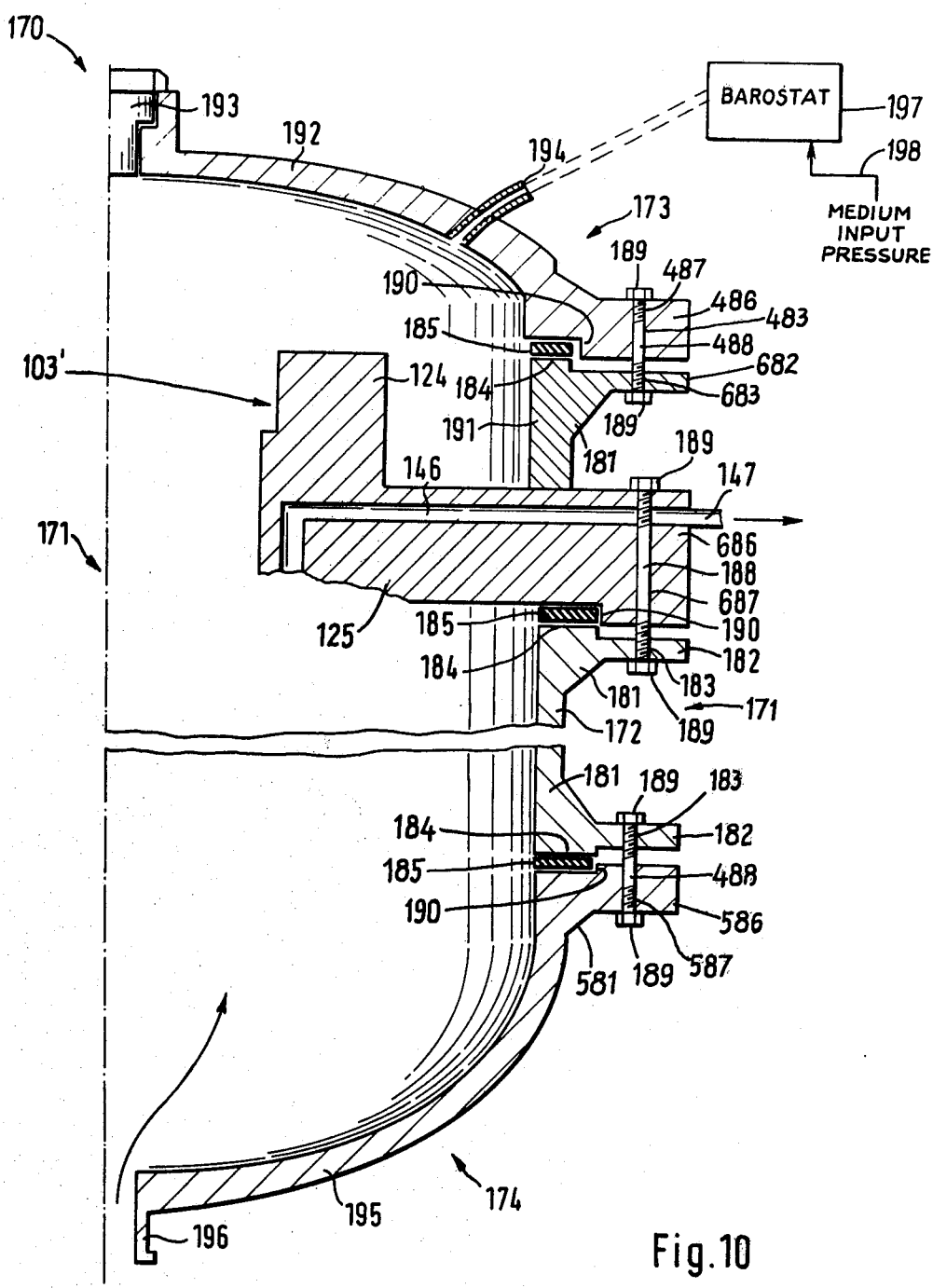
FIG. 10 is a longitudinal section of part of a multichamber photoreactor as in FIG. 9 including pressure balancing equipment.

FIG. 10 shows a modification of three-chamber photoreactor 101 including pressure balancing equipment. Only the components modified over those of three-chamber photoreactor 101 are illustrated in correspondence with FIG. 9 and with specific reference numerals assigned thereto.

Flow reactor 170 of FIG. 10 includes a housing formed by an exterior casing 172, a first closure member 103', and a second closure member 174. Lamp 24 (not shown) and intermediate silica glass tubes 105, 106, 107, also not shown, are designed and arranged as in flow reactor 101.

For connection with closure members 103', 174, both ends of exterior casing 172 have annular flanges 182, which include reinforcements 181 extending around their inner periphery and bores 183 distributed adjacent their outer periphery. Ridges 184 are formed on the ends of annular flanges 182, 682 to cooperate with seals 185 located in recesses 190 formed in respective counterflanges 486, 586, and 686. Counterflange 586 as formed on closure member 174 has a reinforcement 581. Bores 587 and 687 are distributed adjacent the outer periphery of counterflanges 586 and 686, respectively, and correspond in number, position and diameter to bores 183 in annular flanges 182 of exterior casing 172. Similarly, flanges 486 and 682 have aligned bores 483 and 683. Threaded bolts 188, 488 extend through the aligned openings and firmly and pressure-tightly interconnect the same by means by nuts 189.

Closure member 103' is provided at counterflange 686 with axial portions in the same way as closure member 103, only a part of axial portion 125 being shown. Said axial portions are identical to axial portions 124, 125 of flow reactor 101 and like those serve to retain silica glass tubes 105, 106, 107; neither they (nor the glass tubes) being represented in detail in FIG. 10. Like flange 116 counterflange 686, also, has two diametrically opposed interior radial passages 146 opening into the circumferential surface of counterflange 686 and ending in connections 147.

At the face remote from exterior casing 172 counterflange 686 carries an annular projection 191 formed integrally therewith or secured thereto and to which a further closure member 173 comprising a domed cover 192 having a counterflange 486 is flanged pressure-tightly as described hereinbefore. Cover 192 includes a central, pressure-proof, high voltage and flash-over proof passage 193 for the connecting lines of lamp 24. A connection 194 provides for attaching a conduit to a barostat (a pressure regulator for maintaining a constant pressure) 197 which is of commercial design and, therefore, will not be described in detail. A conduit 198 leads to the medium input line (e.g., connection 196 or 147) of the reactor so that the set point of the pressure regulation is established by the input pressure.

Closure member 174 comprises a dome-shaped cover 195 having a central connection 196 and provided with counterflange 586 for connection to the other annular flange 182 of exterior casing 172 as described hereinbefore. A ring 153 (not shown) is supported on the inside of cover 195 and on the ring a perforated plate 155 rests as in flow reactor 101.

During operation, pressurized gas, preferably an inert gas like nitrogen, argon, or carbon dioxide, is supplied from the barostat to flow reactor 171 via connection 194. By means of the barostat a pressure will be generated and maintained which is equal to the internal pressure prevailing within flow reactor 171. Thus pressure differences will be prevented from occurring at silica glass tubes 105, 106, 107 which may result in mechanical strains and fractures in the silica glass tubes.

Figure 11:
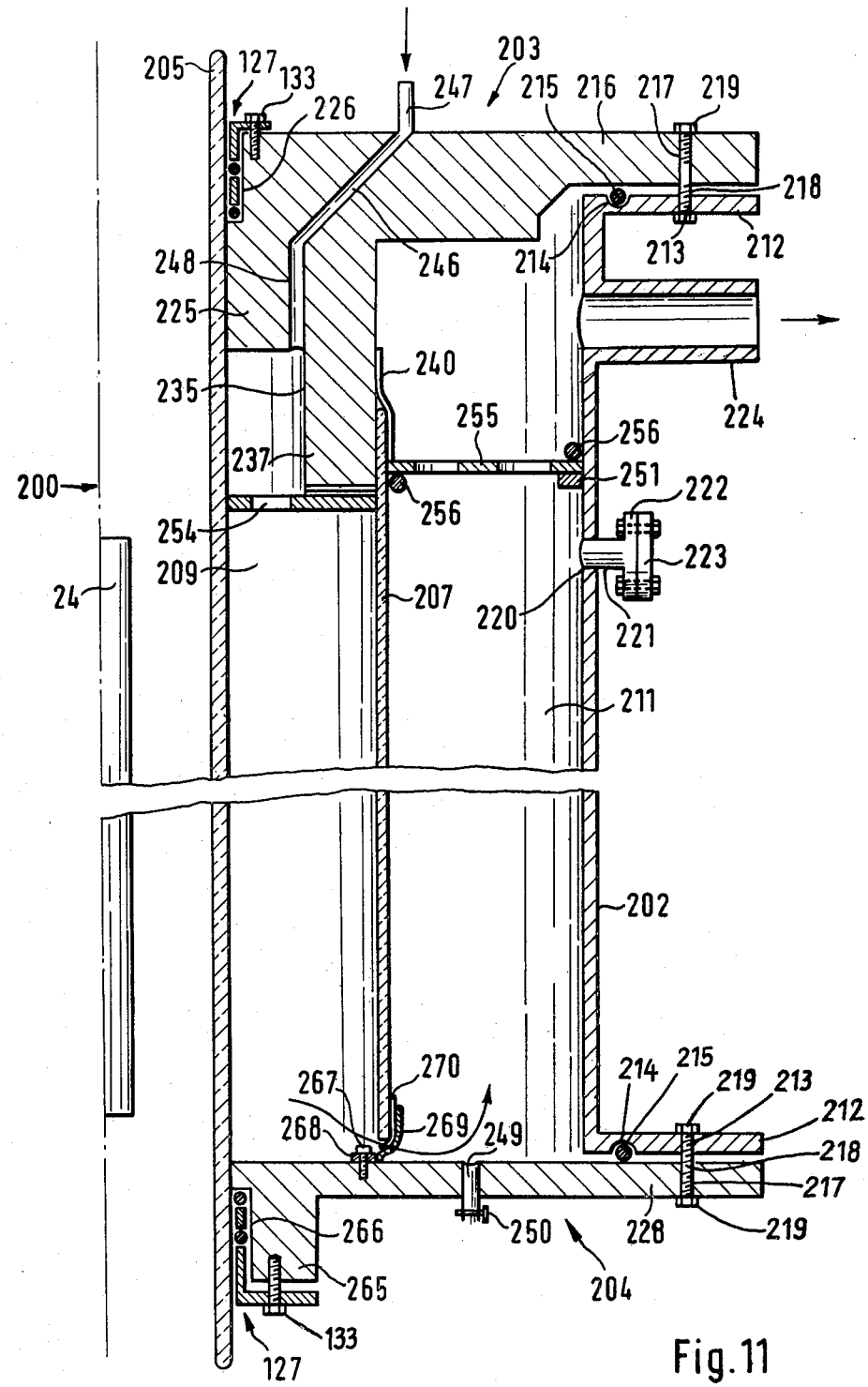
FIG. 11 is a longitudinal section of a fourth embodiment of the multichamber photoreactor according to the invention.

FIG. 11 shows a further embodiment of a multichamber photoreactor essentially differing from three-chamber photoreactor 100 by the numer of irradiation chambers and by the design of the envelope tube. Here a two-chamber photoreactor 200 is shown in the same presentation as three-chamber photoreactor 100 in FIG. 9.

Flow reactor 200 includes a housing formed by an exterior casing 202 opaque to the radiation, a first closure member 203, a second closure member 204 and a transparent interior envelope tube 205 retained at both closure members 203, 204. Interior envelope tube 205 is an open-ended silica glass tube. The flow reactor 200 is subdivided into two irradiation chambers 209, 211 by means of an intermediate silica glass tube 207 retained in closure members 203, 204 at both its ends. Tube 207 forms a window between chambers 209, 211 through which ultraviolet radiation may pass.

For connection to closure members 203, 204 exterior casing 202 has annular flanges 212 at both its ends. The flanges have bores 213 distributed adjacent their periphery. At the end faces of annular flanges 212 there are recesses 214 to receive sealing O-rings 215. Closure members 203, 204 include flanges 216 and 228 with bores 217 distributed adjacent their periphery. Exterior casing 202 and closure members 203, 204 are firmly and sealingly interconnected by bolts 218 extending through bores 213, 217, 228 and secured by nuts 219.

As in the case of the exterior casing 102 of three-chamber photoreactor 100 in FIG. 9, exterior casing 202 has, for purposes of observation and control, an observation port formed by an opening 220 within which is mounted a tube 221 carrying an annular flange 222 and a cover 223. Cover 223 may be silica glass when the port is used for observation purposes. Exterior casing 202 has a lateral connection 224 in a part thereof adjacent to closure member 203. Exterior casing 202, closure members 203, 204 and tubes 205, 207 are made of the same material as the corresponding components in three-chamber photoreactor 100.

Closure members 203, 204 are of generally annular design, the internal diameter being closely adapted to the outer diameter of envelope tube 205. Closure member 203 has an axial portion 225 extending from the interior periphery of flange 216 into the interior space of flow reactor 200 and serving to retain envelope tube 205 and silica glass tube 207 at one end of the flow reactor. From its outer face closure member 203 is provided with a counter bore 226 into which a packing gland 127 is inserted and is secured to the outside of closure member 203 by screws 133. The packing gland firmly and sealingly holds envelope tube 205. At the interior end axial portion 225 is provided with an annular groove 235 defined radially externally by an annular web 237. The outer diameter of axial portion 225 is closely adapted to the internal diameter of silica glass tube 207 so that one end thereof is slipped over the same. A sealing collar 240 held by tube or hose clamps (not shown) surrounds the free part of axial portion 225 and the end of silica glass tube 207. Thus the respective end of silica glass tube 207 will be firmly and sealingly retained at closure member 203.

Closure member 203 has a passage 246 ending in connection 247. At its interior end passage 246 connects with an axial passage 248 extending through axial portion 225 and opening into the base of annular groove 235. Thus communication is provided between connection 247 and interior irradiation chamber 209.

Closure member 204 has an axial portion 265 extending from the interior periphery of flange 228 at the side thereof remote from flow reactor 200. This axial portion serves to retain envelope tube 205 at the other end of flow reactor 200. In its outer face closure member 204 has a counterbore 266 into which a packing gland 127 is inserted. The packing gland is secured to the outside of closure member 204 by screws 133. The gland firmly and sealingly holds envelope tube 205 at this respective end of flow reactor 200. At the inner face of closure member 204 a ring 268 is secured by screws 267. Spring blades 269 project from said ring 268 in a crown-like arrangement and are arched externally to guide a protective cover 270 surrounding the adjacent end of silica glass tube 207. Closure member 204 has an axially extending drain passage 249 connecting the exterior irradiation chamber 211 to a drain valve 250 at the outside of flange 228.

The flow between connections 224 and 247 through two-chamber photoreactor 200 passes through irradiation chambers 209 and 211 communicating through the intermediate spaces between the spring blades 269 and corresponding gaps in cover 270. To generate a uniform flow pattern perforated plates 254, 255 like those in three-chamber photoreactor 100 are provided. Perforated plate 254 is secured to web 237 of closure member 203 and acts upon the flow passing through the interior irradiation chamber 209. Perforated plate 255 abuts a ring 251 secured to the interior wall of exterior casing 202 which ring may also be formed integrally therewith; and at the inside, the plate 255 engages the end face of sealing collar 240. Retaining rings 256 secure perforated plate 255 against displacement. Plate 255 acts upon the flow passing through exterior irradiation chamber 211.

In a preferred embodiment two-chamber photoreactor 200 as illustrated in FIG. 11 comprises an interior irradiation chamber 209 having a depth of d=2.4 cm (measured radially) and an exterior irradiation chamber 211 having a depth of d=4.6 cm. The outer diameter of envelope tube 205 is 7.2 cm, the wall thickness of each of silica glass tubes 205 and 207 is 0.4 cm and the transmission of silica glass at 254 nm of such thickness is T(0.4 cm)=0.92. Within envelope tube 205 there is positioned an antimony doped high pressure xenon lamp 24 (Original Hanau Quarzlampen GmbH, Hanau, Federal Republic of Germany). Such lamp has a strong radiation flux in the range between 260 and 280 nm and supplies 100 W of such radiation at the irradiated interior wall of envelope tube 205 to the medium over an effective length of 80 cm of the irradiated surface of irradiation chamber 209. In an analogous way as compared to foregoing Table 5 the following Table 6 will give values for throughputs Q-40 of two-chamber photoreactor 200 having an overall depth of d=7 cm and of a single-chamber photoreactor having the same depth for media with transmission factors T(1 cm)=0.9 to 0.6, as well as enhancement factors F in the throughput Q-40 of two-chamber photoreactor 200 as compared to that of the aforementioned single-chamber photoreactor.

TABLE 6

Comparison of Throughputs of Two-Chamber Photoreactor 200 and of a Single-Chamber Photoreactor having the same Depth (d = 7 cm) for Media of Various Transmission Factors.

| T (1 cm) | | 0.9 | 0.8 | 0.7 | 0.6 |
|---|---|---|---|---|---|
| Q-40 Two-Ch. | $m^3/h$ | 27.8 | 16.4 | 9.8 | 5.9 |
| Q-40 Single-Ch. | $m^3/h$ | 20.18 | 8.85 | 3.47 | 1.18 |

TABLE 6-continued

Comparison of Throughputs of Two-Chamber Photoreactor 200 and of a Single-Chamber Photoreactor having the same Depth (d = 7 cm) for Media of Various Transmission Factors.

| T (1 cm) | 0.9 | 0.8 | 0.7 | 0.6 |
|---|---|---|---|---|
| F | 1.38 | 1.85 | 2.85 | 5.0 |

100 W of ultraviolet radiation of 260-280 nm in axial position; envelope tube $D_i$ = 7.2 cm.

The data of Table 6 are given with inclusion of account for the transmission of silica at 254 nm to facilitate comparison with throughput values of the same photoreactors equipped with low pressure mercury lamps. However, transmission of silica in the range of 260-280 nm is higher resulting actually in an increase in the values of Q-40 as given in Table 6.

At depths (measured radially) of d=2.4 cm for interior irradiation chamber 209 and d=4.6 cm for exterior irradiation chamber 211 corresponding to an overall depth of d=7 cm two-chamber photoreactor 200 will be provided for high throughputs Q-40 within the range of transmission factors like T(1 cm)=0.7 essential for the disinfection of potable water. As comparison of throughputs in Table 6 will show, enhancement factors of F=1.55 can be achieved by using two irradiation chambers in the range of transmission factors T(1 cm)=0.85 to 0.7. In view of the intended throughputs Q-40 a higher number of irradiation chambers is dispensed with; for the same reason, the outer diameter of envelope tube 205 should not be too small. Two-chamber photoreactor 200 is particularly suited for the purposes of water disinfection in the production of beverages as well as for ultraviolet disinfection in the supply of potable water.

For continuous operation, the direction of flow through two-chamber photoreactor 200 is hardly significant. Generally, flow from the interior irradiation chamber 209 through the exterior irradiation chamber 211 will be preferred. Only in the case of deposit formation reverse direction of flow may be employed, if desired. Due to the instantaneous starting properties of the lamps practically no disadvantageous starting effects ensue even after interruptions in the operation of two-chamber photoreactor 200. In general the more rapid flow of the medium through multi-chamber photoreactors provides for efficient cooling of high power lamps which otherwise would require additional water cooling or the like.

Figure 12:
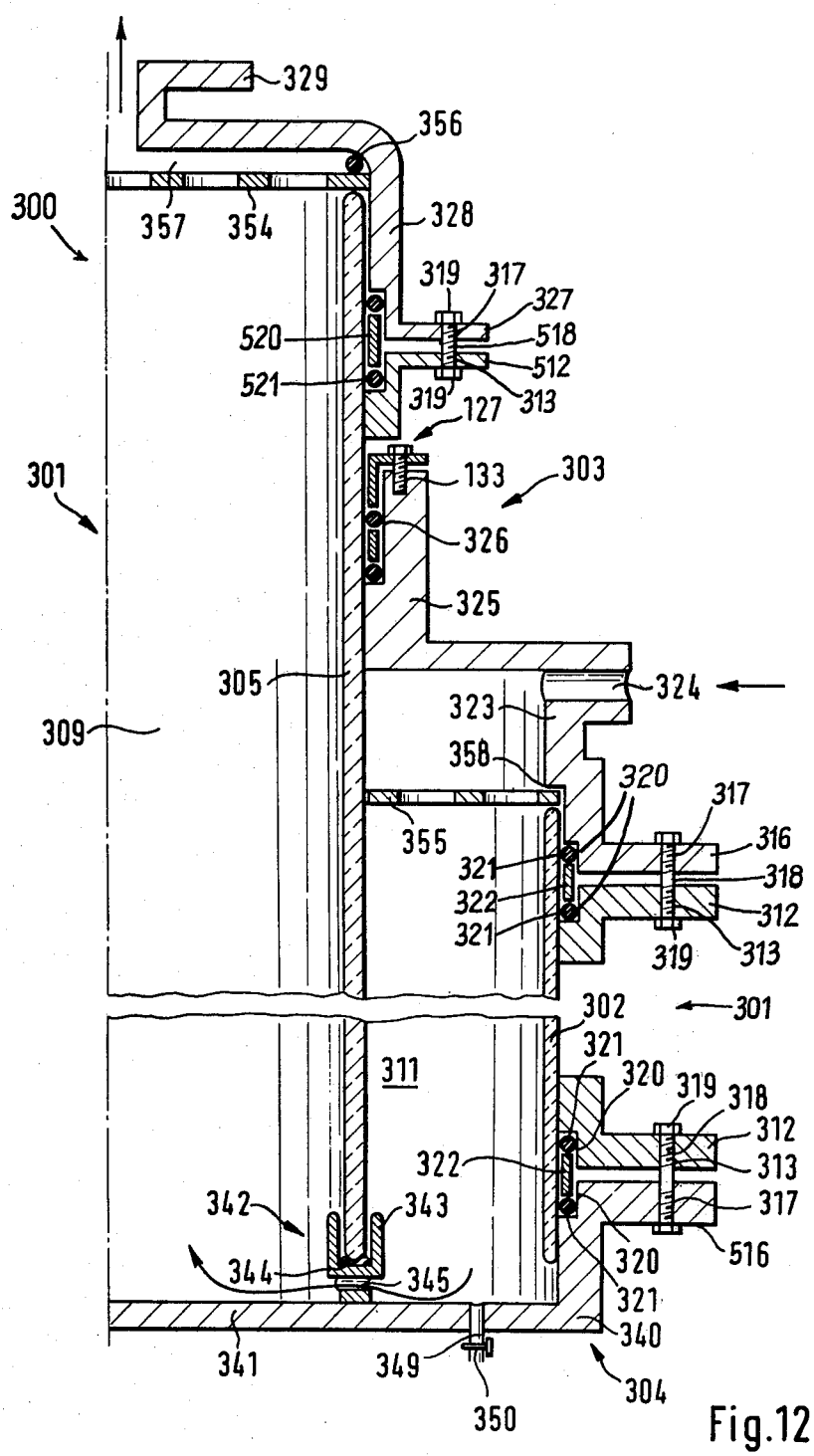
FIG. 12 is a longitudinal section of a part of a fifth embodiment of a multichamber photoreactor according to the invention.

Another embodiment of a two-chamber photoreactor is illustrated in FIG. 12. This has exterior irradiation by a radiation source (not shown) which comprises fourteen low pressure mercury lamps (NN 30/89, Original Hanau Quarzlampen GmbH, Hanau, Federal Republic of Germany). Each lamp is located in a respective paraboloidal reflector and the fourteen lamp-reflector combinations are positioned concentrically relative to a flow reactor 300. The whole arrangement is enclosed by an opaque enclosure (not shown) incorporating also power supplies, control elements and the monitoring equipment for the operation of the two-chamber photoreactor 300. Such radiation sources and housing constructions are known and available commercially (WEDECO, Gesellschaft für Entkeimungsanlagen, Düsseldorf, Herford, Federal Republic of Germany) and their detailed description is not necessary.

Flow reactor 300 includes a housing formed by a transparent exterior tube 302 made of silica glass, retaining means 303, and a closure member 304. An intermediate tube 305 made of silica glass subdivides flow reactor 300 into two irradiation chambers and forms a window for the passage of ultraviolet radiation therebetween.

Exterior tube 302 is connected to retaining means 303 and closure member 304, respectively, by means of annular flange elements 312 located adjacent the ends of the tube. Flange elements 312 have bores 313 angularly spaced adjacent their periphery. Retaining means 303 and closure member 304 each have annular flanges 316 and 516 with bores 317 aligned with bores 313 in annular flange elements 312. Annular flange elements 312, retaining means 303 and closure member 304 are interconnected by threaded bolts 318 secured by nuts 319. The interior of flange members 312, 316 and 516 fit closely to the exterior of tube 302. At the inside they have opposing annular recesses 320 against the bases of which O-rings 321 are pressed by means of guiding sleeves 322. Thus the exterior tube 302 is held firmly and sealingly. Retaining means 303, closure member 304 and interior tube 305 consist of the same material as the corresponding members of two-chamber photoreactor 200.

Retaining means 303 is formed as an axially stepped ring the first step 323 of which fits closely to the outside of exterior tube 302. It has an inner shoulder 358 and fluid connections 324. The inside of the second step 325 thereof fits closely to the outside of interior tube 305 and has a counterbore 326 into which a packing gland 127 is inserted. The packing gland is secured to the outside of retaining means 303 by screws 133 to firmly and sealingly hold the interior tube 305 to retaining means 303. Above retaining means 303 another annular flange element 512 is located to which an adaptor 328, having a counterflange 327, is correspondingly and firmly as well as sealingly connected by threaded bolts 518 and nuts 319 with the interposition of O-rings 521 and sleeve 520. Adaptor 328 fits closely to the outside of interior tube 305 and extends some way beyond the end thereof to taper off to connection 329.

Closure member 304 includes an axially extending ring carrying flange 516, said ring being firmly connected to or formed integrally with a plate 341 closing the end of flow reactor 300. On its inside plate 341 carries a ring 342 secured thereto or formed integrally therewith and terminating in a bifurcated annulus 343 of U-shaped cross-section. Ring 342 extends below and concentrically with interior tube 305, annulus 343 being adapted to the dimensions of the tube so as to guide the same at the end (with the interposition of a protective elastic ring 344). There are passage openings 345 distributed circumferentially about ring 342 to provide communication between irradiation chambers 309 and 311. Plate 341 is provided with an axially extending drain passage 349 connecting the exterior irradiation chamber 311 to a drain valve 350 at the outside of plate 341.

The flow between connections 324 and 329 through two-chamber photoreactor 300 is directed through irradiation chambers 309 and 311 which communicate through passage openings 345 in ring 342. To generate a uniform flow pattern perforated plates 354 and 355 are provided which are designed as in three-chamber photoreactor 100. Perforated plate 354 bears against the end of interior tube 305 and is held by snap ring 356. A back space 357 is formed between connection 329 of adaptor 328 and perforated plate 354. Plate 354 acts upon the flow passing through interior irradiation chamber 309. Perforated plate 355 is retained between the end of exterior tube 302 and the shoulder 358 formed at the first step of retaining means 303. It acts upon the flow passing through exterior irradiation chamber 311.

The preferred embodiment of two-chamber photoreactor 300 as represented in FIG. 12 has an exterior irradiation chamber 311 with a depth of 2.5 cm (measured radially) and an interior irradiaton chamber 309 having an internal diameter of 9.2 cm. The outer diameter ($D_a$) of exterior tube 302 is 15.8 cm. The wall thickness of silica glass tubes 302 and 305 is 0.4 cm and the transmission of silica glass of such thickness at 254 nm is T(0.4 cm)=0.92. The fourteen low pressure mercury lamps referred to and in paraboloidal reflectors will supply a mean irradiation power of 85 W of ultraviolet power at 254 nm distributed over the circumference of exterior tube 302 at an effective length of 79 cm of irradiation chamber 311. The following Table 7 gives values for the throughputs Q-40 of two-chamber photoreactor 300 and of a single-chamber photoreactor provided with an analogous external radiation source comprising six low pressure mercury lamps of the same kind, said single-chamber photoreactor having an inner diameter of D=7 cm, as well as values of Q-40 normalized to 15 W of ultraviolet radiation power at 254 nm, all for various transmission factors T(1 cm) in the range of 0.9 to 0.6. Table 7 also gives enhancement factors F as based on said normalized throughputs Q-40.

TABLE 7

Comparison of Throughputs of Two-Chamber Photoreactor 300 and a Single-Chamber Photoreactor having External Radiation Sources

| T (1 cm) | | 0.9 | 0.8 | 0.7 | 0.6 |
|---|---|---|---|---|---|
| Q-40 Two-Ch. 300 (14 × 11 W UV) | m³/h | 30.5 | 24.2 | 16.1 | 9.5 |
| Q-40 Two-Ch. 300 normalized to 15 W UV | m³/h | 2.97 | 2.38 | 1.57 | 0.91 |
| Q-40 Single-Ch. (6 × 11 W UV) | m³/h | 5.91 | 5.84 | 5.65 | 4.72 |
| Q-40 Single-Ch. normalized to 15 W UV | m³/h | 1.34 | 1.31 | 1.28 | 1.06 |
| F | | 2.21 | 1.85 | 1.23 | 0.85 |

Low pressure mercury Lamps 11 W UV-254 nm in concentric arrangement.
Two-Chamber Photoreactor 300: 14 Lamps; $D_a$ = 15.8 cm.
One-Chamber Photoreactor: 6 Lamps; D = 7 cm.

Two-chamber photoreactor 300 has thus been compared to a cylindrical single-chamber photoreactor having an external radiation source and proved in practice. Such single-chamber photoreactors cannot be built with greater diameters because of the risk of flow short circuits. The application of an external source of radiation is an alternative to the installation of higher-powered axial radiation sources for increasing the output of such photoreactors and offers considerably enhanced yields with respect to time and space, i.e., higher throughputs at unchanged unit volume. Although photoreactors of such design are much less disadvantageous with respect to radiation intensity gradients over the reactor cross-section because of their positive irradiation geometry, even here the principle of subdividing the irradiation chamber offers significantly higher efficiencies.

In practical operation the direction of flow through two-chamber photoreactor 300 will have no significance.

Uses of two-chamber photoreactor 300 for purposes of purification are presented in the following examples:

1. Elimination of Residual Ozone from Water

Ozonized water with a residual ozone contents of 0.3 g/m³ (0.3 ppm) is conducted through two-chamber photoreactor 300 at a throughput Q-40=40 m³/h. The water entering into interior irradiation chamber 309 after leaving exterior irradiation chamber 311 is practically free of ozone (<0.02 ppm); detection by Palin's reagent or, respectively, by colorimetrical analysis (diethyl-p-phenylene diamine and potassium iodide).

2. Removal of Aromatic Hydrocarbons from Water

An emulsion prepared from about 10 g of an aromatic tar oil and 70 m³ of water corresponding to the capacity of a swimming pool contains about 0.13 mg/l aromatic compounds as detected by their characteristic ultraviolet absorption. The water is circulated through a sand filter pack at a rate of 25 m³/h. There is no change in the concentration of aromatic compounds (ultraviolet absorption). If a two-chamber photoreactor 301 is series connected to the sand filter pack, aromatic impurities no longer can be detected in the discharge from the photoreactor (UV absorption; 5 cm cell).

A further increase in the output of two-chamber photoreactor 300 may be achieved by adding an internal radiation source. Such a photoreactor will be obtained in a simple way by just combining the respective components of the photoreactors as illustrated in FIGS. 11 and 12, so that its structure does not have to be described in detail here. An antimony doped high pressure xenon lamp is used as the internal radiation source which may be singly or multiply reversed on itself; mercury vapor lamps of appropriate emission ranges are used as external radiation sources. Such lamps are available commercially.

Further modifications in the structure of flow reactors 1, 20, 40, 100, 200, or 300 will result from the use of a number of other known retaining and guiding means for the partitions subdividing the reactor chamber which are in part differently designed and which are available to the expert. Such elements may be used instead of those represented in FIGS. 1 to 12. Also, in many cases provision of only one lateral connection 147, 224, or 324, respectively, will suffice.

Another problem exists in all those applications in which the irradiated medium is withdrawn discontinuously or in which the withdrawal is interrupted for some periods of time with a constant and high degree of minimum performance in terms of purification or disinfection degree still being required. In such cases a multichamber photoreactor of the kind as shown in FIGS. 9 to 12 is employed and operated in a recirculation mode. FIG. 13 schematically depicts a flow diagram for recirculational operation of three-chamber photoreactor 100; but which also may be used with multichamber photoreactors like 200, or 300, respectively. Also, a two-chamber photoreactor 40 may be employed; although it is intended to be used for water circulated in connection with an air conditioner, and is less suited than the first mentioned photoreactors for flow disinfection with partial recirculation.

The flow diagram of FIG. 13 includes three-chamber photoreactor 100 with the connection 152 thereof being connected by a supply conduit 401 and a supply valve 402 to a reservoir (not shown) holding the fluid medium to be irradiated. A flow rate limiter 12 is series connected to supply valve 402. Connection 147 is connected to recirculating means 407 and to discharge valve 408 through a flow divider 403 having an air vent 424 by means of conduits 404, 405 each of which are equipped with a flow indicator 406. Recirculating means 407 comprises a one-way, constant output recirculation pump 409, a series connected one-way valve 410 and a conduit 411 equipped with a flow indicator 406 and opening into supply conduit 401 between supply valve 402 and flow limiter 12. Instead of one-way pump 409 a recirculation pump of adjustable output may be used. Also, if desired, an adjustable flow restrictor may be provided in recirculating means 407. The entire volume of recirculating means 407 is kept small as compared to that of the multichamber photoreactor associated therewith.

Flow divider 403 as illustrated in FIG. 14 is similar to a pressurized overflow regulator. The sectional representation in FIG. 14 shows a vessel 420 having a valved air vent 424 on top and a supply connector 421 for connection to conduit 147 to three-chamber photoreactor 100. Supply connector 421 projects through the bottom of vessel 420 into the interior thereof. A first discharge connector 422 extends from the bottom of vessel 420 for connection to conduit 404 leading to recirculating means 407. A second discharge connector 423 is above the mouth of supply connector 421 within vessel 420 and connects to conduit 405 leading to discharge valve 408.

In describing the operation of the unit as illustrated in FIGS. 13 and 14 it is assumed that the equipment is completely filled with the respective medium, that the air is vented therefrom and that supply valve 402, discharge valve 408 and air vent 424 are initially closed.

With the discharge valve 408 closed and one-way pump 409 running, the medium will be circulated in a closed loop. The medium enters irradiation chamber 111 of three-chamber photoreactor 100 via conduit 411 and connection 152 and leaves the same (after having passed through irradiation chambers 110 and 109 successively) via connection 147. The medium will then enter the interior of vessel 420 through connector 421. It leaves the flow divider 403 via the first discharge connector 422 and thence through conduit 404 to the input of pump 409.

Discharge valve 408 and supply valve 402 are connected to be operated by valve operator 412 so that they operate together. Valve operator 412 may be one of any known mechanical, electric, hydraulic, pneumatic means or the like. Upon the valves being both opened the medium to be irradiated flows to three-chamber photoreactor 100 for irradiation and the irradiated medium is displaced from the irradiation loop system through open discharge valve 408 in correspondence to the volume of non-irradiated medium supplied through open supply valve 402. Since the medium as supplied will be diluted by the recirculated, already disinfected, medium before introduction into three-chamber photoreactor 100, a medium having a lower germ number will enter the photoreactor resulting in a lower germ number on discharge from the same. It should be noted that by recirculating the medium, the already highly purified recirculating medium will be subjected to further irradiation in a mixture containing non-irradiated medium which altogether implies an alteration in efficiency. At such mode of operation, therefore, the flow rate should be decreased, as compared to a non-recirculating operation, which decrease will be a function of the proportion recirculated.

To improve the efficiency when operating in the recirculation mode it is, however, more expedient to add the medium to be disinfected discontinuously in small amounts and pass the same through. This is done by displacing, on a batch basis, a large portion of the reactor contents during a dwell period while recirculation is stopped, followed by another period of recirculation, and thus irradiation, which in dependence on dose requirements may involve multiple passes of the reactor volume. Therefore another controlled valve 414 (see FIG. 13a) is added in the recirculating line, i.e., conduits 404, 411, and connected to valve operator 412 to operate valve 414 synchronously, but in opposite mode of operation, to discharge valve 408 and supply valve 402. Valves 402 and 408 stay open (and valve 414 in the recirculating line is closed) until the required portion of nonirradiated medium has filled the photoreactor and the irradiated medium has left the same. Upon the closing of valves 402 and 408, valve 414 in the recirculating line opens and the recirculation is resumed with irradiation of the recirculating medium until the next following charge period. Continuous flow of disinfected medium can then be achieved by connecting discharge valve 408 to an intermediate holding tank 416 equipped with a level control and a discharge connection 417 via a flow rate limiter (not shown).

Discontinuous supply of the medium is achieved most simply by means of a controlled metering pump 418, the metered volumes of which are just smaller than the reactor volume. The valve operator 412 is then connected via line 419 to be controlled by the energizing of the metering pump so that valves 402, 408 are closed when the pump is stopped and opened when the pump is energized. With a positive displacement pump 418, valve 402 may be dispensed with as it no longer becomes necessary since the pump itself serves as a valve means. The level control as mentioned before with reference to the continuous discharge equipment including intermediate holding tank 416 may also be utilized to vary the dosage periods and thus the mean varying requirements within the given limits of apparatus power. Thus intended increases in the applied dose can be achieved while maintaining the full function of a given photoreactor.

In purifications and disinfections by ultraviolet irradiation utilizing the recirculation mode just described it is recommended that the multichamber photoreactors be used so that the medium will pass last through the irradiation chamber having the smallest cross-section and the highest radiation intensity.

Multichamber photoreactors utilizing the simple kind of recirculation are particularly suitable for water disinfection on sea-going vessels. Batch-wise recirculation operation is well suited for applying high doses of radiation to obtain highest degrees of purification or disinfection.

The safety required in achieving the irradiation results as desired is obtained by employing flow control means to prevent the exceeding of a predetermined maximum permitted flow rate of the medium through multichamber photoreactors as shown in FIGS. 1 to 12. In the most simple case a flow restrictor incorporated within the supply conduit to the respective flow reactor will suffice as such a safety element. In cases of variable input pressures an adjustable flow restrictor, for example like a valve, is recommended; however, more reliable flow rate limiters like 12 will be preferred. For safety reasons interposition of such an element should also be made if a pump with adjustable discharge volume is employed the discharge volume of which can be immediately adjusted and even monitored.

Figure 15:
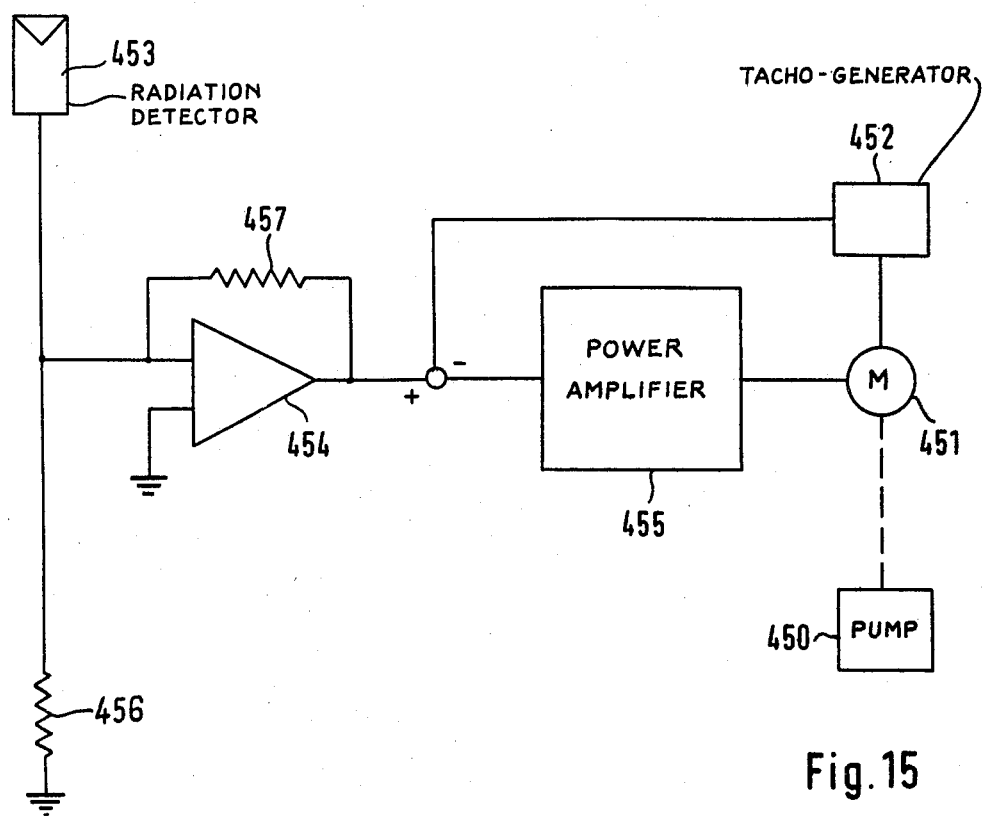
FIG. 15 is a schematic diagram of a detail in the electrical monitoring equipment used in operation of a multichamber photoreactor according to the invention.

The multichamber photoreactors should be provided with monitoring equipment to ensure that a decrease of the radiation intensity below a predetermined set value will initiate an alarm and switch off the irradiation unit altogether. Also, the radiation flux from the source will decrease with time. Because of the exponential dependence of the irradiation result, and thus also of the multichamber photoreactor output, on the radiation intensity continuous control of the flow rate in relation to the instantaneous radiation intensity is necessary for optimum utilization of the radiation emitted by the radiation source. This is accomplished by the apparatus diagrammatically illustrated in FIG. 15.

A pump 450 having an adjustable discharge volume is connected to the input of a flow reactor (e.g., 100, 200, or 300). A control unit adjusts the discharge volume of the pump in accordance with the respectively prevailing radiation intensity. The control unit comprises a tacho-generator 452 driven by the pump motor 451, a radiation sensitive detector 453 connected to ground via leakage resistor 456 and attached to look inwardly through tube 121 or 221 of flow reactor 100 or 200, respectively, or to the interior tube 302 of flow reactor 300 (using an appropriately designed passage), and an amplifier 454 supplied with the output signal of detector 453 and having a feedback resistor 457. The output signals of tacho-generator 452 and amplifier 454 are fed with opposed signs to the input of a power amplifier 455 and the amplified differential voltage obtained at the output thereof is supplied to pump motor 451. As the radiation received by the detector 453 decreases the motor 451 is slowed down (or the motor speed is increased with an increase in detected radiation). Thus the discharge volume of pump 450 is adapted to the prevailing radiation intensity by a control unit composed entirely of commercially available components.

In the multichamber photoreactors 100, 200, and 300, the respective irradiation chambers are series connected with respect to the direction of flow passing therethrough. Such connection has particular advantages related to better mixing of the medium and to the passage thereof through all the irradiation chambers of the photoreactor. In specific cases parallel connection of the irradiation chambers may be advantageous, particularly in the treatment of media having high transmission factors.

Flow reactors of the type as shown in FIGS. 11 and 12 are readily modified to form separate irradiation chambers adapted for parallel flow as will be seen in FIGS. 16 and 17. The modified form of two-chamber photoreactor 200 consists of a flow reactor 501 surrounding the ultraviolet radiation source 24 and essentially comprising two irradiation chambers 509 and 511 each of which has inlet and outlet connections. FIG. 16 illustrates a longitudinal section through the top half of flow reactor 501. The lower half of the reactor is essentially similar thereto in a mirror image relationship.

Flow reactor 501 has an exterior casing 202A which differs from exterior casing 202 of flow reactor 201 essentially by the presence of another diametrically opposed pair of connections 224 near the lower annular flange 212 not shown in FIG. 16. There is, however, only one opening 220 for observation purposes into which a tube 221 carrying an annular flange 224 and a cover 223 is inserted.

At both of its ends, flow reactor 501 is closed by identical cover members, generally 503, and intermediate flange members, generally 504, to which cover members 503 are fastened as by screw bolts 506 extending through flanges 516 thereof. Intermediate flange members 504 have flanges 490 with bores 491 distributed adjacent their periphery. Exterior casing 202A and intermediate flange members 504 are firmly and sealingly interconnected by bolts 218 extending through bores 491, 217 and secured by nuts 219. Sealing rings 215 therebetween are located in annular recesses 214.

Each of the cover members 503 is generally of annular design and extends axially from an outer end adapted closely to the outer diameter of envelope tube 205 to an inner end adapted closely to the outer diameter of silica glass tube 207. At the outer end is a counter bore 526 into which a packing gland 127 is mounted. This gland is secured to the end flange by means of bolts 533 and serves to firmly and sealingly hold the envelope tube 205. In an intermediate region, between the axial ends, the axial portion of each cover member 503 widens to a size to accommodate silica glass tube 207 at its lower end. The widened axial portion has two diametrically opposed connections 524 to pass the medium to be irradiated through the interior irradiation chamber 509. The interior wall of the widened axial portion forms a shoulder 552 close to connections 524. This shoulder positions a perforated plate 554 held in place by a retaining ring 553. The inner axial end of each cover member 503 extends beyond flange 516 for a purpose subsequently described.

Each intermediate flange member 504, also, is of generally annular design and comprises a flange portion 490 and an axial portion 537 with an internal diameter closely adapted to the outer diameter of silica glass tube 207. The axial portion 537 has a counter bore 536 of a length to receive the inner axial end of cover member 503 and a packing gland. This gland comprises two sealing rings 538, 540 and a guiding bush 539. This arrangement, together with flange 516 of cover member 503 which is secured by screw bolt 506 to flange 490 of intermediate flange member 504, serves to firmly and sealingly hold silica glass tube 207. The end face of the axial portion 537 is chamfered inwardly to facilitate centered introduction of silica glass tube 207 while the flow reactor is being assembled. The chamfered end of axial portions 537 of the intermediate flange members 504 do not extend into the region of connections 224 to ensure that the flow of the medium through exterior irradiation chamber 511 is not obstructed thereby. The interior wall of casing 202A has an annular shoulder 251 closely adjacent to connections 224. This shoulder positions a perforated plate 254 secured by a retaining ring 253.

The members of flow reactor 501 are constructed from the same material as the corresponding members of flow reactor 201.

The embodiment of FIG. 16 forms two paths for the fluid medium to flow through the reactor. One path is from connections 524 in the illustrated upper half of the reactor, through chamber 509 (between tubes 205 and 207) and to the connections 524 in the non-illustrated lower half of the reactor. The other path is from connections 224 in the upper half, through chamber 511 (between tube 207 and casing 202A) and to the connections 224 in the lower half. Of course, the flow may be in either direction between the connections.

FIG. 17 illustrates the upper part of a flow reactor 301A similar to that of FIG. 12, but having two flow paths. Flow reactor 301A is used with an external radiation source, not shown. The non-illustrated lower part of flow reactor 301A is essentially in a mirror image of the illustrated upper part relationship and each is identical to that portion of flow reactor 301 shown above the break lines in FIG. 12. Therefore, no further description of the structure will be required. The two diametrically opposed pairs of connections 324 in the upper part from inlets and the two corresponding connections in the lower part form outlets (or vice versa) for irradiation chamber 311. The central connections 329 in the top and bottom parts form the inlet and outlet of irradiation chamber 309. Utilization of such flow reactors having irradiation chambers connected in parallel will be found in connections with reverse osmosis plants which are employed in numerous applications for the preparation of pure water (for example potable water from sea water) in hospitals for specific purposes, electronics laboratories, pharmaceutical factories and in the food industry. In reverse osmosis various types of membranes, often based on organic materials, are usually employed. Those organic materials have been proven to be prone to the growth of micro-organisms which endanger operability of the plants as well as the hygienic quality of the water produced. For safety reasons, therefore, ultraviolet disinfection units will often be series connected to reverse osmosis plants. However, it will be expedient to already subject the medium entering the reverse osmosis plant to ultraviolet disinfection to limit the growth of micro-organisms on the membranes. In such cases two-chamber photoreactors having parallel connected irradiation chambers will offer a technically specifically favorable solution for simultaneously disinfecting the initial medium as well as the produced water using one reactor and one radiation source.

To further increase the photochemical efficiency in the purification or disinfection it is recommended in irradiation systems comprising irradiation units connected in parallel to design at least one of said units like a multichamber photoreactor with series connected irradiation chambers as described hereinbefore.

I claim:

1. An apparatus for purifying a fluid medium and comprising a continuous flow reactor defining a radiation chamber having two sides and through which chamber said medium flows, and an ultraviolet radiation source positioned to introduce ultraviolet radiation into the medium in said chamber at one of said sides, said chamber having a depth between said sides such that some of the incident radiation is not absorbed by the medium in said chamber, said reactor including first means forming a window transparent to ultraviolet radiation at the other of said sides of said chamber and, at the other side of said window from said chamber, second means forming a second reaction chamber for the flow of medium therethrough to be acted upon by the radiation passing through said window into said second chamber, said apparatus characterized by:

the relationship between said medium, the strength of the incident radiation and said depth is established such that the radiation received at said window is at least fifty percent of the incident radiation;

said reactor having a total number n, less than six, of successive series-connected reaction chambers and windows therebetween through which windows radiation will pass from one chamber to the next;

the relationship between the strength of the incident radiation, the character of the media in the chambers and the depth of the chambers being such that the total radiation absorbed by the media in all of the chambers does not exceed $(1-0.5^n) \cdot 100$ percent of the total incident radiation; and the relationship between the rate of flow of the medium through all the reaction chambers and the radiation intensity effective in each reaction chamber being established so that the sum of the fractional doses applied to the medium in each one of the reaction chambers equals a predetermined minimum radiation dose.

2. An apparatus as set forth in claim 1, wherein said one of said sides of said chamber comprises an annular tube transparent to ultraviolet radiation and defining an enclosure;

wherein said first means comprises an annular shell concentric with said tube to define said first mentioned chamber between said tube and said shell, said shell being transparent to ultraviolet radiation and forming said window, said first means defines fluid passage openings at each end of said first mentioned chamber;

wherein said second means comprises a fluid retainer about said shell with said second reaction chamber being within said retainer and about said shell;

wherein said source is positioned within said tube;

wherein said fluid retainer is a window transparent to ultraviolet radiation; and including a second source of ultraviolet radiation comprising a number of UV lamps and reflectors arranged on a circle surrounding said window forming said fluid retainer to emit ultraviolet radiation toward the same.

3. An apparatus as set forth in claim 2, wherein one of said sources comprises mercury lamp means and the other of said sources comprises antimony doped xenon lamp means.

4. An apparatus as set forth in claim 2, wherein plate means are provided in the first and in the second reaction chamber, said plate means extending normal to the axis of the respective chamber for producing a uniform pattern of flow therethrough.

5. An apparatus as set forth in claim 2, wherein the enclosure, the annular shell and the fluid retainer are sealingly retained each at both their ends in coaxial arrangement in first and second closure means each having an axial opening therethrough;

wherein the first of said closure means includes an annular portion concentric with said fluid retainer and projecting into the interior thereof, said annular portion having a given external diameter;

wherein the annular shell has an inside diameter substantially corresponding to said external diameter and an end encircling said annular portion, and wherein the annular shell is retained at said annular portion by a sealing collar engaging one end of said shell and said annular portion and at the second of the closure means by a plurality of spring blades supporting said shell against displacement, said blades being spaced to permit fluid flow between the reaction chambers.

6. An apparatus as set forth in claim 1, wherein said one of said sides of said chamber comprises an annular tube transparent to ultraviolet radiation and defining an enclosure;

said first means comprises an annular shell concentric with said tube and sealed thereto at its top end to define said first mentioned chamber between said tube and said shell, said shell being transparent to ultraviolet radiation and forming said window, said first means defines fluid passage openings at each end of said first mentioned chamber;

said second means comprises a fluid retainer about said shell with said second reaction chamber being within said retainer and about said shell; and said retainer is a tank of a size sufficient to receive a plurality of shells corresponding in size to that of said annular shell, and said tube and shell are positioned vertically within said tank, said tube being closed at the bottom thereof, one of said fluid passage openings being at the bottom of said first means and opening into the interior of the tank and the other one of said fluid passage openings forming connection means located adjacent the top end of said shell, the connection means of the plurality of shells present in said tank being interconnected to form a common fluid inlet or fluid outlet as the case may be.

7. An apparatus as set forth in claim 1,
wherein said first means comprises an annular shell concentric with said tube to define said first mentioned chamber between said tube and said shell, said shell being transparent to ultraviolet radiation and forming said window, said first means defines fluid passage openings at each end of said first mentioned chamber;

wherein said second means comprises a fluid retainer about said shell with said second reaction chamber being within said retainer and about said shell;

wherein said source is positioned within said tube;

wherein said second means includes an annular wall concentric with and outside of said shell and closure members at each end of said wall; and wherein said first means defines an internal passage between the two chambers and comprising one of said openings, and said second means defines another passage opening communicating with the second reaction chamber, whereby the medium may be passed through the two chambers in series.

8. An apparatus as set forth in claim 1, wherein said reactor has an input connection and an outlet connection between which the medium flows through the reactor, and further characterized by including:
a recirculation device having two ends and for providing recirculation of said medium from said outlet connection to said input connection, first connection means connecting one of said ends to said input connection, and second connection means connecting the other of its ends to said outlet connection.

9. An apparatus as set forth in claim 8, including an intake conduit connected to said first connection means upstream from said input connection and downstream of said recirculating device, said first connection means including a rate of flow control device downstream of said intake conduit and said recirculating device.

10. An apparatus as set forth in claim 1, and including a device for establishing a rate of flow of medium through said chambers, said apparatus further characterized by said device being:

a flow rate limiter operating independently of pressure.

11. Apparatus as set forth in claim 1,
wherein said one of said sides of said chamber comprises an open top of a generally horizontal tank having two ends; wherein said first means includes a plate extending horizontally through said tank to define said first reaction chamber between said top and said plate, said plate being transparent to ultraviolet radiation and forming said window, said first means defines fluid passage openings at each end of said tank;

wherein said second means comprises a bottom of said tank extending between said two ends to define said second reaction chamber between said window and said bottom, said second means defines fluid passage openings at each end of said tank;

wherein said source is positioned above said top and comprises a number of UV lamps and reflectors arranged to emit substantially parallel ultraviolet radiation toward said tank;

wherein said first means includes first connecting means forming one of said fluid passage openings associated with said first reaction chamber at one end thereof and passage means forming the other one of said fluid passage openings of said first reaction chamber at the opposite end thereof; and wherein the first of said closure means includes an axial portion concentric with said fluid retainer, said axial portion concentric with said fluid retainer, said axial portion sealingly retaining the enclosure and the second tube at their respective open end and the shell at one of its ends;

wherein the first of said closure members includes connecting means forming one of the fluid passage openings associated with the first reaction chamber;

wherein the other free end of said shell ends at an axial distance from the closed end of said second tube to define the other of said fluid passage openings of said first reaction chamber and one of the fluid passage openings associated with the second reaction chamber;

wherein the second tube has passage means adjacent the end retained in said axial portion, said passage means forming the other of said fluid passage openings of said second reaction chamber and one of the fluid passage openings associated with the third reaction chamber; and wherein said second closure members includes connecting means forming the other of said fluid passage openings of said third reaction chamber.

12. An apparatus as set forth in claim 11,
wherein fluid level controlling means are provided to establish the level of the fluid medium in the tank, said fluid level controlling means being adjustable to permit variations in the level of said medium in said tank.

13. An apparatus as set forth in claim 12,
wherein the fluid level controlling means is connected to the outlet connecting means and comprises a vessel having a vented top and a discharge tube extending into the vessel, said discharge tube having an upper intake opening and being vertically adjustable for providing said variations in the level of the fluid medium in the tank.

14. An apparatus as set forth in claim 12, wherein the fluid level controlling means comprise a flow rate limiter operating independently of pressure, said flow rate limiter being connected to the inlet connecting means.

15. An apparatus as set forth in claim 11, wherein the first and second reaction chambers are provided with plate means extending normal to the axis of the respective chamber for producing a uniform pattern of flow therethrough.

16. An apparatus as set forth in claim 1, wherein said one of said sides of said chamber comprises a first tube closed at one end and transparent to ultra-violet radiation, said tube defining an enclosure;
wherein said first means comprises an annular shell concentric with said enclosure to define a first reaction chamber between said enclosure and said shell, said shell being transparent to ultraviolet radiation and forming a first window, said first means defines fluid passage openings at each end of said first reaction chamber;
wherein said second means includes a second tube concentric with said shell to define a second reaction chamber between said shell and said second tube, said second tube being transparent to ultraviolet radiation and forming a second window, said second means defines fluid passage openings at each end of said second reaction chamber;
wherein third means are provided including a fluid retainer about said second tube to define a third reaction chamber between said second tube and said retainer, said second means defines fluid passage openings at each end of said third reaction chamber;
wherein said source is positioned within said enclosure; and
wherein said fluid retainer forms an annular wall concentric with and outside of said enclosure, said shell and said second tube and said third means include closure members at each end of said wall.

17. An apparatus as set forth in claim 16, wherein the fluid retainer is sealingly closed at both of its ends by first and second closure members;
wherein the first of said closure means includes an axial portion concentric with said fluid retainer, said axial portion concentric with said fluid retainer, said axial portion sealingly retaining the enclosure and the second tube at their respective pen end and the shell at one of its ends;
wherein the first of said closure members includes connecting means forming one of the fluid passage openings associated with the first reaction chamber;
wherein the other free end of said shell ends at an axial distance from the closed end of said tube to define the other of said fluid passage openings of said first reaction chamber and one of the fluid passage openings associated with the second reaction chamber;
wherein the second tube has passage means adjacent the end retained in said axial portion, said passage means forming the other of said fluid passage openings of said second reaction chamber and one of the fluid passage openings associated with the third reaction chamber; and
wherein said second closure members includes connecting means forming the other of said fluid passage openings of said third reaction chamber.

18. Apparatus as set forth in claim 17 wherein plate means are provided in at least the third reaction chamber, said plate means extending normally to the axis of said chamber for producing a uniform pattern of flow therethrough.

19. An apparatus as set forth in claim 1, wherein said first means comprises an annular shell to define said first reaction chamber, said shell being transparent to ultraviolet radiation and forming said window, said first means defines fluid passage openings at each end of said first mentioned chamber;
wherein said second means comprises a fluid retainer about said shell with said second reaction chamber being within said retainer and about said shell;
wherein said fluid retainer is a window transparent to ultraviolet radiation concentric with an outside of said shell and closure members at each end of said fluid retainer; and
wherein said source comprises a number of UV lamps and reflectors arranged on a circle surrounding said window forming said fluid retainer to emit UV radiation toward the same.

20. An apparatus as set forth in claim 19, wherein plate means are provided in the first and in the second reaction chamber, said plate means extending normal to the axis of the respective chamber for producing a uniform pattern of flow therethrough.

21. An apparatus as set forth in claim 19, wherein the enclosure, the annular shell and the fluid retainer are sealingly retained each at both their ends in coaxial arrangement in first and second closure means each having an axial opening therethough;
wherein the first of said closure means includes an annular portion concentric with said fluid retainer and projecting into the interior thereof, said annular portion having a given external diameter;
wherein the annular shell has an inside diameter substantially corresponding to said external diameter and an end encircling said annular portion, and
wherein the annular shell is retained at said annular portion by sealing collar engaging one end of said shell and said annular portion and at the second of said closure means by support means receiving the respective end of said shell to prevent displacement thereof and having passage means to provide communication between the reaction chambers.

22. An apparatus as set forth in claim 1, wherein said reactor comprises:
a housing including an annular exterior tube, closure members at each end of said tube, and means interengaging said tube and members, said housing defining an interior space, said housing being pressure tight, and
an annular intermediate silica glass tube within said space, coaxial with the first mentioned tube and dividing said space into said radiation chambers, said intermediate tube forming said window between said chambers; and
including pressure balancing means communicating with the interior of said housing.

23. An apparatus as set forth in claim 1, wherein the depths of the chambers are such that, for a given radiation intensity from said source and for a given medium, and approximately equal proportion of the respectively incident radiation is absorbed by the medium in each irradiation chamber.

24. An apparatus as set forth in claim 1, wherein there are at least three chambers with the chambers, in the order that they are traversed by the radiation from said source, having successively greater depths.

25. An apparatus for purifying a fluid medium and comprising a continuous flow reactor defining a radiation chamber having two sides and through which chamber said medium flows, and an ultraviolet radiation source positioned to introduce ultraviolet radiation into the medium in said chamber at one of said sides, said chamber having a depth between said sides such that some of the incident radiation is not absorbed by the medium is said chamber, said reactor including first means forming a window transparent to ultraviolet radiation at the other of said sides of said chamber and, at the other side of said window from said chamber, second means forming a second reaction chamber for the flow of medium therethrough to be acted upon by the radiation passing through said window into said second chamber, said apparatus characterized by:
  the relationship between said medium, the strength of the incident radiation and said depth is established such that the radiation received at said window is at least fifty percent of the incident radiation;
  said reactor having a total number n, less than six, of successive series-connected reaction chambers and windows therebetween through which windows radiation will pass from one chamber to the next;
  the relationship between the strength of the incident radiation, the character of the media in the chambers and the depth of the chambers of the media in the chambers and the depth of the chambers being such that the total radiation absorbed by the media in all of the chambers does not exceed $(1-0.5^n) \cdot 100$ percent of the total incident radiation;
  the relationship between the rate of flow of the medium through all the reaction chambers and the radiation intensity effective in each reaction chamber being established so that the sum of the fractional doses applied to the medium in each one of the reaction chambers equals a predetermined minimum radiation dose;
  and including a device for establishing a rate of flow of medium through said chambers, said apparatus further characterized by:
  said second means forming an observation port at a location at which the radiation traversing both chambers will impinge on said port;
  radiation sensing means at said port for receiving and measuring the amount of unabsorbed radiation traversing both chambers and producing a signal indicative thereof; and
  control means connected to said sensing means and said device for adjusting the rate of flow of the medium to increase the flow as the unabsorbed radiation increases and to decrease the flow as the unabsorbed radiation decreases to obtain an optimum throughput of medium while ensuring that the medium receives a minimum radiation dose.

26. An apparatus as set forth in claim 25 and wherein said device is a pump having a motor, the further improvement wherein said control means comprises:
  means connected to said device for producing a signal indicative of the speed of said pump; and
  amplifier means connected to the last mentioned means, the sensing means and the motor for adjusting the speed of said motor as a function of the difference of said signals.

27. An apparatus for purifying a fluid medium and comprising a continuous flow reactor defining a radiation chamber having two sides and through which chamber said medium flows, and an ultraviolet radiation source positioned to introduce ultraviolet radiation into the medium in said chamber at one of said sides, said chamber having a depth between said sides such that some of the incident radiation is not absorbed by the medium in said chamber, said reactor including first means forming a window transparent to ultraviolet radiation at the other of said sides of said chamber and, at the other side of said window from said chamber, second means forming a second reaction chamber for the flow of medium therethrough to be acted upon by the radiation passing through said window into said second chamber, said apparatus characterized by:
  the relationship between said medium, the strength of the incident radiation and said depth is established such that the radiation received at said window is at least fifty percent of the incident radiation;
  said reactor having a total number n, less than six, of successive series-connected reaction chambers and windows therebetween through which windows radiation will pass from one chamber to the next; said reactor having an input connection and an outlet connection between which the medium flows through the reactor;
  the relationship between the strength of the incident radiation, the character of the media in the chambers and the depth of the chambers being such that the total radiation absorbed by the media in all of the chambers does not exceed $(1-0.5^n) \cdot 100$ percent of the total incident radiation;
  the relationship between the rate of flow of the medium through all the reaction chambers and the radiation intensity effective in each reaction chamber being established so that the sum of the fractional doses applied to the medium in each one of the reaction chambers equals a predetermined minimum radiation dose;
  a recirculation device having two ends and for providing recirculation of said medium from said outlet connection to said input connection, first connection means connecting one of said ends to said input connection, and second connection means connecting the other of its ends to said outlet connection;
  an intake conduit connected to said first connection means upstream from said input connection and downstream of said recirculating device, said first connection means including a rate of flow control device downstream of said intake conduit and said recirculating device; and
  said recirculation device including a recirculating pump and a one-way valve means permitting flow in only one direction through said recirculating device.

28. An apparatus as set forth in claim 27, including a discharge conduit with valve means connected to the second connection means, an intake conduit with valve means connected to said first connection means, and operating means interconnecting said valve means and said device for providing recirculation when said valve means are blocking the flow therethrough and stopping said recirculation when said valve means are permitting flow therethrough.

29. An apparatus as set forth in claim 27, including a discharge conduit with valve means connected to the second connection means, operating means interconnecting said valve means and said device, a supply pump connected to said intake conduit, said pump operating intermittently for supplying medium intermittently to said input connection, said pump being connected to said operating means for opening said discharge conduit valve means and to said recirculation device for stopping recirculation when said pump is operating and closing said discharge conduit valve means and providing recirculation when said pump is stopped.

30. An apparatus as set forth in claim 27, wherein said recirculating pump is adjustable as to its pumping capacity.

31. An apparatus as set forth in claim 27, including a discharge conduit, and wherein said second connection means includes a flow divider means having an input connected to said outlet connection, a first outlet connected to said recirculating device, and a second outlet connected to said discharge conduit.

32. An apparatus for purifying a fluid medium and comprising a continuous flow reactor defining a radiation chamber having two sides and through which chamber said medium flows, and an ultraviolet radiation source positioned to introduce ultraviolet radiation into the medium in said chamber at one of said sides, said chamber having a depth between said sides such that some of the incident radiation is not absorbed by the medium in said chamber, said reactor including first means forming a window transparent to ultraviolet radiation at the other of said sides of said chamber and, at the other side of said window from said chamber, second means forming a second reaction chamber for the flow of medium therethrough to be acted upon by the radiation passing through said window into said second chamber, said apparatus characterized by:

the relationship between said medium, the strength of the incident radiation and said depth is established such that the radiation received at said window is at least fifty percent of the incident radiation;

said reactor having a total number n, less than six, of successive series-connected reaction chambers and windows therebetween through which windows radiation will pass from one chamber to the next wherein said reactor comprises:

a housing including an annular exterior tube, closure members at each end of said tube, and means interengaging said tube and members, said housing defining an interior space, said housing being pressure tight, and an annular intermediate silica glass tube within said space, coaxial with the first mentioned tube and dividing said space into said radiation chambers, said intermediate tube forming said window between said chambers; and including pressure balancing means communicating with the interior of said housing, the relationship between the strength of the incident radiation, the character of the media in the chambers and the depth of the chambers being such that the total radiation absorbed by the media in all of the chambers does not exceed $(1-0.5^n)\cdot 100$ percent of the total incident radiation;

the relationship between the rate of flow of the medium through all the reaction chambers and the radiation intensity effective in each chamber being established so that the sum of the fractional doses applied to the medium in each one of the reaction chambers equals a predetermined minimum radiation dose; and said pressure balancing means including a barostat and a conduit connecting the barostat to the medium input to the reactor so that the set point of the pressure regulation by the barostat is determined by the medium input pressure.

* * * * *

UNITED STATES PATENT AND TRADEMARK OFFICE
CERTIFICATE OF CORRECTION

PATENT NO. : 4,317,041    Page 1 of 3
DATE : Feb. 23, 1982
INVENTOR(S) : Günther O. Schenck It is certified that error appears in the above-identified patent and that said Letters Patent are hereby corrected as shown below:

Col. 2, l. 59     "ad" should be -- äd --

Col. 6, l. 33     "and" should be -- are --

Col. 8, l. 67     In last column heading, under "0.6", insert -- $m^3/h$ --

Col. 10, Table 1

Col. 11, l. 16     "silicon" should be -- silica --

Col. 16, l. 5     "Consequently" should be -- Correspondingly --

Col. 18, l. 4     "113" should be -- 112 --

Col. 18, l. 53     "125" should be -- 126 --

Col. 20, Table 5     In right hand column, third item down, "2.10-" should be -- $2.10^{-5}$ --

Col. 36, l. 29 through l. 53

Delete:
"wherein the first of said closure means includes an axial portion concentric with said fluid retainer, said axial portion concentric with said fluid retainer, said axial portion sealingly retaining the enclosure and the second tube at their respective open end and the shell at one of its ends;
wherein in the first of said closure members includes connecting means forming one of the fluid passage openings associated with the first reaction chamber;
wherein the other free end of said shell ends at an axial distance from the closed end of said second tube to define the other of said fluid passage openings of said first

UNITED STATES PATENT AND TRADEMARK OFFICE
CERTIFICATE OF CORRECTION

PATENT NO. : 4,317,041

DATED : Feb. 23, 1982

INVENTOR(S) : Günther O. Schenck

It is certified that error appears in the above-identified patent and that said Letters Patent are hereby corrected as shown below:

reaction chamber and one of the fluid passage openings associated with the second reaction chamber;
wherein the second tube has passage means adjacent the end retained in said axial portion, said passage means forming the other of said fluid passage openings of said second reaction chamber and one of the fluid passage openings associated with the third reaction chamber;
and
wherein said second closure members includes connecting means forming the other of said fluid passage openings of said third reaction chamber." and insert:
-wherein said second means includes second connecting means forming one of said fluid passage openings associated with said second reaction chamber at one end thereof associated with said first connecting means and passage means forming the other one of said fluid passage openings of said second reaction chamber at the opposite end thereof, whereby said passage means provide fluid communication between said first and said second reaction chambers and said connecting means provide for an inlet and an outlet connection to

UNITED STATES PATENT AND TRADEMARK OFFICE
CERTIFICATE OF CORRECTION

PATENT NO. : 4,317,041

DATED : Feb. 23, 1982

INVENTOR(S) : Günther O. Schenck

It is certified that error appears in the above–identified patent and that said Letters Patent are hereby corrected as shown below:

| | |
|---|---|
| Col 37, l. 49 | the respective one of said chambers. - "pen" should be - open - |
| Col. 37, l. 55 | before "tube", insert - second - |
| Col. 39, l. 13 | "is" should be - in - |

Signed and Sealed this

Third Day of August 1982

[SEAL]

Attest:

GERALD J. MOSSINGHOFF

*Attesting Officer*  *Commissioner of Patents and Trademarks*